(12) United States Patent
Thomas

(10) Patent No.: US 8,069,998 B2
(45) Date of Patent: Dec. 6, 2011

(54) SURGICAL HOLDER FOR A SURGICAL CONTAINER AND SURGICAL CONTAINER

(75) Inventor: Stefan Thomas, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 408 days.

(21) Appl. No.: 12/215,039

(22) Filed: Jun. 23, 2008

(65) Prior Publication Data
US 2008/0314789 A1 Dec. 25, 2008

(30) Foreign Application Priority Data
Jun. 25, 2007 (DE) .......................... 10 2007 030 863

(51) Int. Cl.
*A47F 7/00* (2006.01)

(52) U.S. Cl. .................. 211/85.13; 211/86.01; 206/370; 206/477

(58) Field of Classification Search ............... 211/85.13, 211/60.1, 65, 66, 69, 69.1, 69.2, 69.9, 70.4, 211/70.6, 70.7, 70.8, 85.25, 133.6, 96, 99, 211/168, 184; 206/438, 214, 1.7, 305, 349, 206/362, 363, 364, 365, 366, 368, 369, 370, 206/477; 312/209; 248/220.31, 220.41, 248/220.42, 220.43, 222.12
See application file for complete search history.

(56) References Cited

U.S. PATENT DOCUMENTS

| | | | | |
|---|---|---|---|---|
| 3,751,575 A * | 8/1973 | Barb | .............................. | 174/485 |
| 4,135,868 A * | 1/1979 | Schainholz | .................... | 422/310 |
| 4,762,688 A * | 8/1988 | Berry, Jr. | ....................... | 422/310 |
| 5,098,676 A | 3/1992 | Brooks, Jr. | | |
| 5,384,103 A * | 1/1995 | Miller | .......................... | 422/310 |
| 5,492,671 A * | 2/1996 | Krafft | .............................. | 422/26 |
| 5,599,512 A | 2/1997 | Latulippe et al. | | |
| 5,681,539 A * | 10/1997 | Riley | ............................. | 422/300 |
| 5,759,502 A * | 6/1998 | Spencer et al. | ............... | 422/300 |
| 6,244,447 B1 | 6/2001 | Frieze et al. | | |
| 6,331,280 B1 * | 12/2001 | Wood | .......................... | 422/300 |
| 6,382,575 B1 * | 5/2002 | Frush et al. | ............. | 248/220.31 |
| 6,419,886 B1 | 7/2002 | Oberdorfer et al. | | |
| 6,629,615 B2 * | 10/2003 | Kim | .......................... | 211/85.13 |
| 6,969,498 B1 * | 11/2005 | Riley | ............................ | 422/300 |
| 2002/0023890 A1 * | 2/2002 | Jensen et al. | .................. | 211/168 |
| 2007/0212277 A1 * | 9/2007 | Riley | ............................ | 422/292 |

FOREIGN PATENT DOCUMENTS

| | | |
|---|---|---|
| DE | 28 12 712 | 9/1979 |
| DE | 20 2005 015 415 | 1/2006 |
| DE | 20 2007 000 931 | 3/2007 |
| WO | 99/44717 | 9/1999 |

* cited by examiner

*Primary Examiner* — Darnell Jayne
*Assistant Examiner* — Stanton L Krycinski
(74) *Attorney, Agent, or Firm* — Lipsitz & McAllister, LLC

(57) ABSTRACT

In order to improve a surgical holder for surgical instruments and/or implants for a surgical container, in particular, a sterile container or perforated basket, comprising a storage device for holding and/or storing surgical instruments and/or implants and an attachment device for attaching the holder to the container, such that it can be attached to the container more easily it is suggested that the attachment device be transferable from an attaching position, in which it can be brought into engagement with and connected to the container, into a position of abutment, in which it can be brought out of engagement with the container, and that the attachment device comprise at least two attachment members, which are connected to one another via the storage device, for attaching the holding to the container. Furthermore, an improved surgical container is suggested.

49 Claims, 17 Drawing Sheets

SURGICAL HOLDER FOR A SURGICAL CONTAINER AND SURGICAL CONTAINER

CROSS-REFERENCE TO RELATED APPLICATION

The present disclosure relates to the subject matter disclosed in German application number 10 2007 030 863.0 of Jun. 25, 2007, which is incorporated herein by reference in its entirety and for all purposes.

FIELD OF THE INVENTION

The invention relates to a surgical holder for surgical instruments and/or implants for a surgical container, in particular, a sterile container or perforated basket, comprising a storage device for holding and/or storing surgical instruments and/or implants and an attachment device for attaching the holder to the container.

Furthermore, the invention relates to a surgical container for the storage and/or sterilization and/or cleaning of surgical instruments and/or implants, comprising a receiving space defined by a base and side walls and at least one holder for surgical instruments and/or implants, wherein the at least one holder comprises a storage device for holding and/or storing surgical instruments and/or implants and an attachment device for attaching the holder to the container.

BACKGROUND OF THE INVENTION

A surgical instrument and/or an implant can be held and/or stored in a defined manner, for example, at a specific position in the receiving space of a surgical container with the aid of a surgical holder of the type described at the outset. A plurality of surgical instruments and/or implants can be neatly arranged in the container. They can also be held at their respective positions when the container is moved and are, therefore, better protected against damage, for example, any impacting on one another.

One example for such a surgical holder is described in the Utility Model No. DE 20 2005 015 415 U1. It comprises, in the form of individual parts, a profiled element for holding and storing instruments as well as attachment elements. The attachment elements abut on the outer wall of a container for attaching this holder to a sterile container, wherein holding arms provided on the attachment elements are each guided through an opening in the container and brought into engagement with the profiled element abutting on the inner wall of the container. The disadvantage of such a holder is the fact that several individual parts have to be handled in order to attach it to the container and that handling, in particular, must occur outside and inside the container.

An object of the present invention is, therefore, to improve a surgical holder for a surgical container and a surgical container of the type described at the outset in that the holder can be attached to the container more easily.

SUMMARY OF THE INVENTION

In a first aspect of the invention, a surgical holder for at least one of surgical instruments and implants for a surgical container comprises a storage device and an attachment device. The storage device is adapted for at least one of holding and storing at least one of surgical instruments and implants. The attachment device is adapted for attaching the holder to the container. The attachment device is transferable from an attaching position, said attachment device being adapted to be brought into engagement with and connected to the container in said position, into a position of abutment, said attachment device being adapted to be brought out of engagement with the container in said position. Attachment device comprises at least two attachment members for attaching the holder to the container. The attachment members are connected to one another via the storage device.

In a second aspect of the invention, the surgical container for at least one of the storage and the sterilization and cleaning of at least one of surgical instruments and implants comprises receiving space defined by a base and side walls and at least one holder for at least one of surgical instruments and implants. The at least one holder comprises a storage device and an attachment device. The storage device is adapted for at least one of holding and storing at least one of surgical instruments and implants. The attachment device is adapted for attaching the holder to the container. The attachment device is transferable from an attaching position, said attachment device being adapted to be brought into engagement with and connected to the container in said position, into a position of abutment, said attachment device being adapted to be brought out of engagement with the container in said position. The attachment device comprises at least two attachment members which are connected to one another via the storage device.

BRIEF DESCRIPTION OF THE DRAWINGS

The foregoing summary and the following description may be better understood in conjunction with the drawing figures, of which.

DETAILED DESCRIPTION OF PREFERRED EMBODIMENTS OF THE INVENTION

Figure 1:
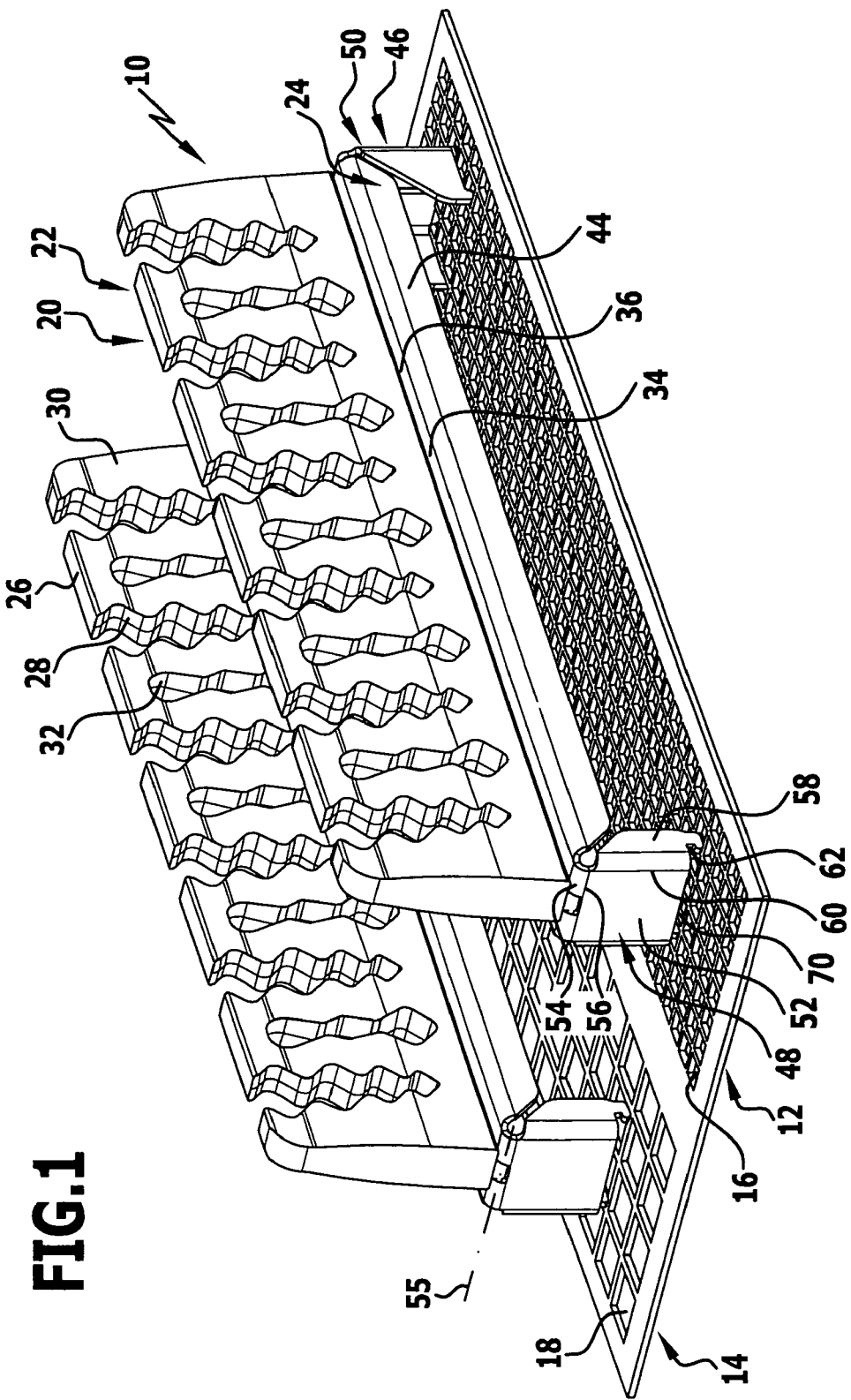
FIG. 1: shows a perspective view of a first embodiment of two surgical holders according to the invention, each attachable to a base of a surgical container according to the invention.
Figure 2:
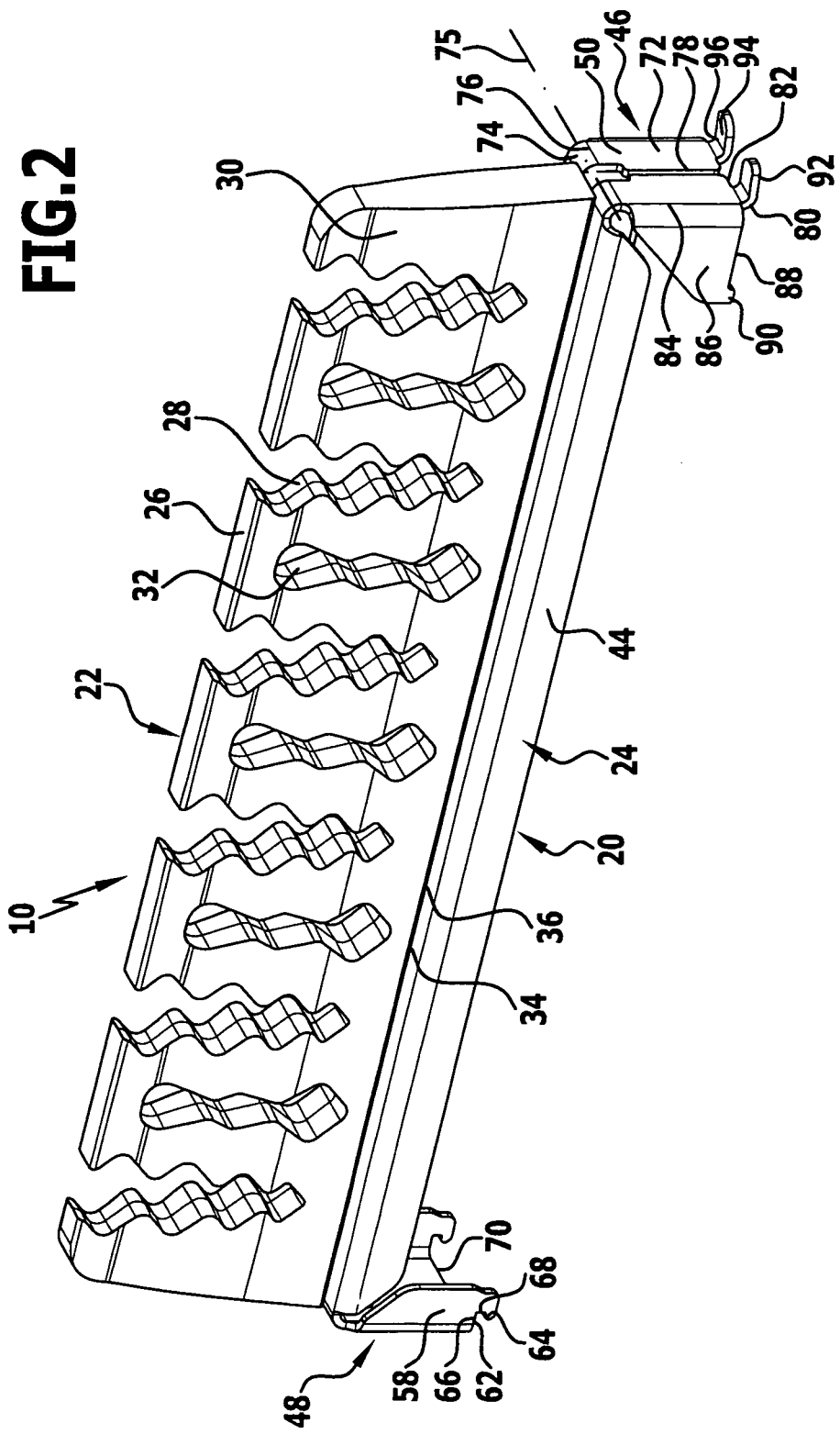
FIG. 2: shows a perspective view of one of the holders from FIG. 1.
Figure 3:
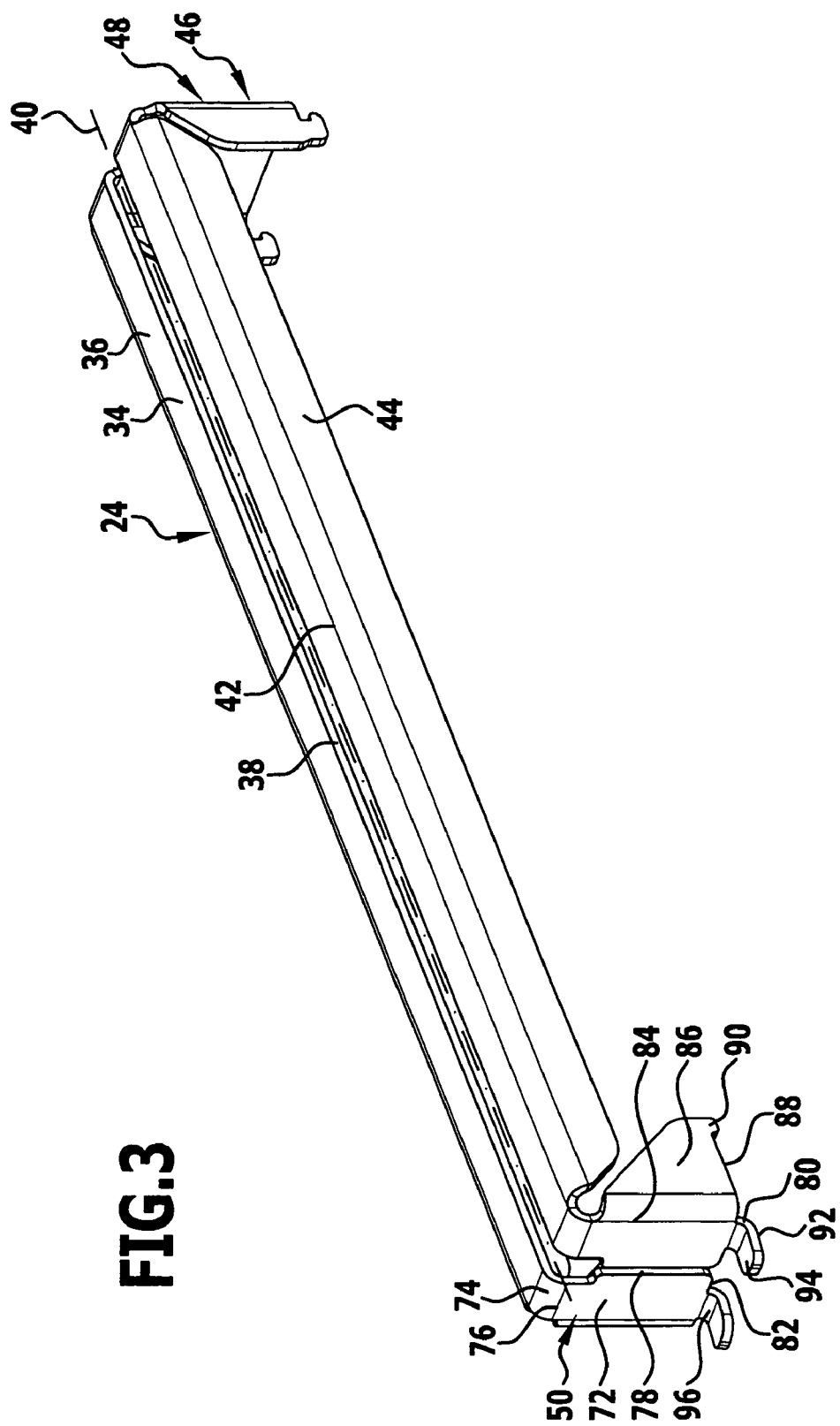
FIG. 3: shows a perspective view of an attachment device and a holding part of a storage device of one of the holders from FIG. 1, connected to the attachment device.

Although the invention is illustrated and described herein with reference to specific embodiments, the invention is not intended to be limited to the details shown. Rather, various modifications may be made in the details within the scope and range of equivalents of the claims and without departing from the invention.

In accordance with the invention, it is suggested that, in a holder of the type described at the outset, the attachment device can be transferred from an attaching position, in which it can be brought into engagement with and connected to the container, into a position of abutment, in which it can be brought out of engagement with the container, and that the attachment device comprises at least two attachment members, which are connected to one another via the storage device, for attaching the holder to the container.

As a result of the fact that the attachment members are connected to one another via the storage device, the holder can, for example, be brought closer to a side wall or a base from the side of the side wall or the base within the receiving space of a container and attached thereto as a whole, i.e., in particular, the attachment device together with the storage device held thereon. A connection of several individual parts of the holder to one another during their attachment to the container, for example, once the attachment device has engaged through openings provided on the container is not necessary. The operational step of attaching the holder to the container is simplified and can, therefore, be carried out more quickly.

The storage device can be designed in one part or in several parts. In the case of a one-part design of the storage device, the entire holder can also be designed in one part and, where applicable, machined in one piece. In the case of an embodiment with a storage device in several parts, this preferably comprises at least one storage element for holding surgical instruments and at least one holding part for holding the at least one storage element. This offers the possibility of combining different respective holding parts and storage elements with one another. In this case, the attachment members are advantageously connected to one another via the at least one holding part. The at least one storage element can then, for example, be attached to the at least one holding part first of all and, subsequently, the complete holder consisting of its individual parts can be attached to the container in a simple manner.

As a result of the fact that the attachment device can be transferred from the attaching position into the position of abutment, it is possible to repeat the attachment of the holder to the container and the removal of the holder from the container many times without considerable wear and tear occurring. For example, a container which has a plurality of positions suitable for the attachment of the holder can be provided in a flexible manner with holders of different shapes at different positions depending on the number and type of instruments and/or implants to be stored.

At least one of the at least two attachment members is advantageously arranged so as to be movable relative to the storage device and/or to another attachment member. In this case, the transfer of the attachment device from the attaching position into the position of abutment can be brought about by movement of this attachment member relative to the storage device and/or to another attachment member.

The attachment members favorably protrude from the storage device. As a result, they can be guided on the base or a side wall of the container in a simple manner and the attachment procedure will be hindered as little as possible by a possibly voluminous shape of the storage device.

In accordance with a preferred embodiment of the invention, a restoring device can be provided for transferring the attachment device from the position of abutment into the attaching position. When the restoring device is actuated during the attachment of the attachment device to the container, it can be ensured that the attachment device will take up the attaching position and, therefore, be secured to the container in a stable manner and remain on the container.

It is favorable when the restoring device comprises at least one restoring element, which is associated with one of the at least two attachment members, for transferring the attachment device from the position of abutment into the attaching position. In this case, each restoring element can be used to transfer the respective attachment member, with which it is associated, into the position which this takes up when the entire attachment device takes up the attaching position.

The at least one restoring element is preferably designed in the form of an elastically resilient section of the attachment member. As a result, the attaching position can define, in particular, a basic position of the attachment device. The transfer into the position of abutment can be brought about, for example, in that at least one attachment member is deflected contrary to the spring force of its elastically resilient section. The deflecting force must be applied temporarily to keep the attachment device in the position of abutment. It can abut on the container in the position of abutment. When the deflecting force is withdrawn following abutment on the container, the spring force of the elastically resilient section forces the at least one attachment member back into the basic position and, therefore, also into the attaching position. Without any renewed deflection of the at least one attachment member, no release of the attachment device from the container is possible.

A distance between the at least two attachment members is advantageously greater or smaller in the position of abutment than in the attaching position. As a result, the attachment device can be transferred into the position of abutment by a simple movement of the attachment members relative to one another.

It is particularly advantageous when the distance is defined between free ends of the at least two attachment members. When the attachment members have, for example, restoring elements in the form of elastically resilient sections and can be transferred into the position of abutment as a result of deflection of the attachment members contrary to the spring force of the elastically resilient section, the distance defined between their free ends can be increased or decreased in size to a relatively great extent by such a deflection.

At least one of the at least two attachment members preferably comprises at least one coupling element, wherein the at least one coupling element has a first coupling surface, which points towards or essentially towards the storage device, for abutment on a corresponding attachment surface of a surgical container, and wherein the holder has at least one second coupling surface, which points away or essentially away from the storage device, for abutment on at least one, preferably corresponding attachment surface of a surgical container. When the first and the at least one second coupling surfaces each abut in the attaching position on a preferably corresponding attachment surface, the holder cannot be moved by way of pressure or a pulling force which is exerted in the direction of a connecting line between the storage device and the coupling element. When the first and second coupling surfaces extend, for example, parallel to a container base, the holder cannot be removed from the container by means of a pulling force exerted at right angles to the base.

It is advantageous, in particular, when the first coupling surface defines a first coupling plane and the second coupling surface defines a second coupling plane, wherein the first and the second coupling planes are parallel or essentially parallel to one another and wherein the first coupling plane is at a greater distance from the storage device than the second coupling plane. Coupling elements with such a spatial arrangement of the coupling surfaces can be brought into engagement, for example, with webs which are located between openings provided in the container such that the first and the second coupling surfaces of a coupling element abut on surfaces of a web which point away from one another.

In accordance with a preferred embodiment of the invention, it may be provided for the at least one coupling element to be designed in the form of a recess with a first side surface and for the first side surface to define the first coupling surface. The provision of a recess in an attachment member represents a simple method of generating a coupling element.

In a further, preferred embodiment of the invention, it may be provided for the at least one coupling element to be designed in the form of a projection with a first side surface and for the first side surface to define the first coupling surface. Such a projection can also be formed on an attachment member in a simple manner.

In a further, preferred embodiment of the invention, it may be provided for the at least one coupling element to be designed in the form of a curved free end of the at least one attachment member, wherein the curved free end has a first side surface and the first side surface defines the first coupling surface. The at least one coupling element of this embodiment can also be produced in a simple manner.

The at least one second coupling surface can be advantageously provided on the at least one coupling element. As a result, one or more coupling elements can each have, for example, a first and a second coupling surface. The storage device need then not have any additional surface suitable for abutment on an attachment surface of a container. It can, for example, remain spaced from a base of a container after the holder has been attached to the base and so surgical instruments and/or implants but also additional objects, such as, for example, cables, circuit boards or small motors, can be stored and/or held, for example, clamped between the storage device and the base of the container.

The at least one coupling element is advantageously designed in the form of a recess, a projection or a curved free end of the at least one attachment member and has a second side surface, wherein the second side surface defines the at least one second coupling surface. During the production of such coupling elements, a mutual positioning of the first and the second side surfaces which is advantageous for the attachment of the holder to the container can be brought about in a simple manner.

It can also be of advantage when the at least one second coupling surface is provided on the storage device. The holder can be attached to a container in a particularly stable manner when the storage device abuts directly on the container.

It is favorable when the attachment device has at least one abutment surface which extends at right angles or essentially at right angles to the first and/or the second coupling surface and can abut on a preferably corresponding attachment surface of the container in the attaching position. This makes movement of the attachment device attached to the container difficult in a direction pointing towards this preferably corresponding attachment surface. As a result of the provision of two abutment surfaces on the attachment device, which point away or essentially away from one another, the holder can be mounted in the attaching position, for example, between the two corresponding attachment surfaces of the container in such a stable manner that every shifting along the connecting line between the two attachment surfaces is made considerably more difficult.

It is advantageous when the at least one abutment surface is provided on at least one attachment member. Since the attachment device is attached to the container with the aid of the attachment members, it serves the simplicity of the construction when the at least one abutment surface is also provided here. When a coupling element is provided on the at least one attachment member, for example, in the form of a recess, a base surface of the recess can define the abutment surface.

In a preferred embodiment of the invention, it may be provided for the storage device to comprise at least one storage element for holding and/or storing surgical instruments and/or implants and at least one holding part for holding the at least one storage element and for the attachment device to comprise at least two attachment members connected to one another via the at least one holding part. As a result, an exchange of the at least one storage element is, for example, made possible. Storage elements may, for example, be of different shapes in order to be better suited for holding specific surgical instruments and/or implants. One or more holding parts of one or more holders can then be provided with one or more corresponding storage elements dependent on the instruments and/or implants to be held. When the at least one holding part or the at least one storage element is damaged, only the individual part actually involved must be exchanged, not the entire holder. As a result of the fact that the storage device comprises several individual parts, it is, in addition, possible to produce each of the parts from a material suitable for the function of the respective part. For example, the at least one storage element can be manufactured from plastic, whereby fewer scratches and slide marks occur on the surgical instruments and/or implants stored in it, the at least one holding part, on the other hand, from, for example, a metal. It is favorable when the at least one holding part is arranged between the at least two attachment members. A holding part arranged between two attachment members each capable of being attached to a container can be held in its position in a particularly stable manner.

It is advantageous when at least one of the at least two attachment members is angled away from the at least one holding part through a member angle. As a result, it is easier to bring the attachment members up to a base or a side wall of a container.

The holder can easily be brought up to a base or a side wall of a container when the member angle is approximately 20° to approximately 160°. It is particularly favorable when the member angle is approximately 80° to approximately 150°.

In a preferred embodiment of the invention, the at least one holding part is designed in the form of a flat or essentially flat web. As a result, a simple production of a holding part worked in one piece with two attachment members is, for example, made possible. In this respect, two outer sections of a flat strip which are adjacent to a middle section in a longitudinal direction of the strip are angled away from the middle section of the flat strip which consists, for example, of an elastic metal material. The middle section defines the holding part, the outer sections two attachment members of a holder according to the invention.

It is favorable when at least one holding part receptacle is provided on the at least one storage element and the at least one holding part can be brought into engagement with the at least one holding part receptacle. For example, a holding part can be brought into engagement each time with a holding part receptacle in a form-locking and/or force-locking manner so that the at least one storage element is held on the at least one holding part in a stable manner.

In a preferred embodiment of the invention, the at least one holding part receptacle is designed in the form of a holding part opening in the storage element and the at least one holding part can be guided through the at least one holding part opening. A holding part opening can be formed in the storage element in a particularly simple manner. When the holding part opening extends, for example, between two sides of the storage element and a holding part guided through the holding part opening is connected on each of the two sides of the storage element with at least one attachment member, the storage element and the holding part cannot be separated from one another for as long as the holder is attached to the container via the attachment members. The storage element is, therefore, held on the holding part in a stable manner. A holding part designed, for example, in the form of a flat or essentially flat web can be guided through a holding part opening provided in the storage element in a simple manner.

In order to increase the stability of the holder, it may be provided for at least two holding parts to be connected to one another via at least one stabilizing element. For example, components of different shapes, for example, those with H-shaped or U-shaped structures can be obtained as a result of the connection of two web-like holding parts via a likewise web-like stabilizing element dependent on the positions, at which the stabilizing element is connected to the holding parts.

Furthermore, the stability of the holder can also be increased in that at least two attachment members connected to different holding parts are connected to one another via at least one stabilizing element. As a result, the relative positions of these holding parts relative to one another can be determined without the holding parts being connected directly to one another. They can, for example, be brought into engagement with different holding part receptacles of a storage element. A storage element with several holding part receptacles can be held in a flexible manner either on several components which are separate from one another and each comprise a holding part and attachment members connected to the respective holding part or on only one component, in which at least one stabilizing element connects attachment members, which are connected to different holding parts, to one another.

In a preferred embodiment of the invention, it may be provided for the storage device to comprise at least one storage element for holding and/or storing surgical instruments and/or implants and at least one holding part for holding the at least one storage element and for the at least one holding part to be transferable from a holding position, in which the at least one storage element is held on the at least one holding part, into a removal position, in which the at least one storage element and the at least one holding part can be detached from one another. This makes a plurality of possible combinations between different storage elements and holding parts possible. For example, a holding part, dependent on the instruments and/or implants to be held, can be purposefully provided with a storage element which is suitable for holding these instruments and/or implants. Whereas the at least one storage element can be held on the at least one holding part in the holding position in a stable manner, the transferability of the at least one holding part into the removal position offers the possibility of repeating the procedures of the connection and release of the at least one storage element and the at least one holding part many times without considerable wear and tear occurring. Optionally, it may also be provided, in the case of a holder of the type described at the outset, for the storage device to comprise at least one storage element for holding and/or storing surgical instruments and/or implants and at least one holding part for holding the at least one storage element and for the at least one holding part to be transferable from a holding position, in which the at least one storage element is held on the at least one holding part, into a removal position, in which the at least one storage element and the at least one holding part can be detached from one another.

The attachment device can preferably be transferred from an attaching position, in which it can be brought into engagement with and connected to the container, into a position of abutment, in which it can be brought out of engagement with the container. As a result, the attachment device can be attached to the container in a simple manner.

The attachment device preferably comprises, in particular, at least two attachment members connected to one another via the at least one holding part of the storage device. The at least one holding part can then be brought up to and attached to the base or a side wall within the receiving space of a container together with the attachment members and, where applicable, the at least one storage element without any connection of several individual parts of the holder to one another being necessary.

The at least one holding part preferably comprises at least one holding member for holding the at least one storage element in the holding position. Such a holding member can be designed, for example, such that the at least one storage element can be brought into engagement with it in the holding position of the holding part.

The at least one holding part preferably comprises, in particular, at least two holding members. A storage element can be held on a holding part in a more stable manner when it is held, for example, on two or three holding members of the holding part. A storage element can also be clampable between two or three holding members in the holding position.

It is favorable when the at least two holding members are arranged so as to be movable relative to one another. The transfer of a holding part from the holding position into the removal position can, for example, be brought about by movement of at least two holding members of the holding part relative to one another. For example, a storage element can be inserted between two holding members of a holding part in the removal position. During the subsequent transfer of the holding part from the removal position into the holding position, a distance of the holding members relative to one another is reduced. In the holding position, the holding members can, finally, be in engagement with the storage element or clamp the storage element.

The at least two holding members are advantageously arranged so as to be pivotable relative to one another. Also, in the case of holding members connected rigidly to one another, the movability of the holding members relative to one another can be ensured in a simple manner by way of pivotability.

It is favorable when the at least two holding members each have a first end and a second end and are connected to one another at their first ends via a hinged connection. As a result, the holding members can be pivoted relative to one another over the entire extension between their first ends and their second ends. In the removal position, a storage element can be brought up close to a surface of a holding member which extends from the first to the second end of this holding member and held on it in the holding position.

The hinged connection is preferably designed in the form of a simple hinge, a film hinge or a spring hinge. Hinges of this type are technically and comprehensively optimized examples for hinged connections.

In a preferred embodiment of the invention, one attachment member can comprise the hinged connection. As a result, the construction of the holder is simplified considerably. When an attachment member is produced, for example, from an elastically bendable sheet metal and connected to two holding members, the holding members can be moved relative to one another with simultaneous bending of the sheet metal of the attachment member. In addition, an attachment member can, with this configuration, be provided at the first ends of the holding members and, therefore, project advantageously from the storage device for attachment to a container.

An attachment member is advantageously arranged at the second end of at least one holding member. An attachment member can also be arranged at this position in an exposed manner. When a holding member is connected to an attachment member, for example, at each of its first and second ends, each of the two attachment members can easily be guided to a container with one hand and attached to it during attachment of the holder to the container, irrespective of a possibly voluminous shape of the storage device.

The at least one holding member favorably has at least one holding element for holding the at least one storage element in the holding position in a form-locking and/or force-locking manner. As a result, the stability of the support of the at least one storage element on the holding part is increased.

At least one holding element of at least one holding member preferably points towards or essentially towards another holding member. This makes a more stable support of a storage element, which is held by at least two holding members, possible and, in particular, of a storage element which is in engagement with several holding members or clamped between several holding members in the holding position.

In a preferred embodiment of the invention, the at least one holding element can be designed in the form of a projection. One or more projections can be formed on a holding member in a simple manner.

In accordance with a further, preferred embodiment of the invention, the at least one holding element can be designed in the form of a recess. A recess can also be provided on a holding member in a simple manner.

At least one holding member is advantageously designed in the form of a profiled rail. In this case, a storage element can be held in the holding position on a structured surface of the rail, which extends over the entire longitudinal extension of the rail, in a stable manner.

It is favorable when the at least one storage element has at least one connecting element which is held on the at least one holding part in the holding position in a form-locking and/or force-locking manner. In this way, the at least one storage element can be designed such that it is held on the at least one holding part in the holding position in a particularly stable manner.

It is favorable, in particular, when the at least one connecting element is designed to correspond to a holding element of the holding part. As a result, a connecting element and a holding element can be connected to one another each time in the holding position in a form-locking and/or force-locking manner.

The at least one connecting element is preferably designed in the form of a projection or a recess. A connecting element of a storage element designed in the form of a projection can be designed, for example, to correspond to a holding element of a holding member designed in the form of a recess.

The at least one connecting element is advantageously designed in the form of a groove. A groove can be produced in a simple manner and brought into engagement with an elongated projection or also a plurality of projections.

The at least one storage element is, in particular, advantageously designed in the form of a profiled bar. A profiled bar has a plurality of surfaces, on which surgical instruments and/or implants which are of various different shapes can be held.

In a preferred embodiment of the invention, the at least one holding part and the at least two attachment members can be connected non-releasably. As a result, the number of individual parts required for the assembly of a surgical holder according to the invention is reduced.

It is particularly favorable when the at least one holding part and the at least two attachment members are worked in one piece. They can, in this case, be produced together, for example, in an injection molding or shaping step.

In a preferred embodiment of the invention, the holder can be produced at least partially from a metal. For example, at least one holding part and the attachment device can be produced in one piece in a simple manner in that a model is punched from a flat metal sheet in a punching step and the model is bent or folded into the desired shape in subsequent shaping steps. When the sheet metal consists of an elastic metal material, a restoring element of the holder which is designed in the form of an elastically resilient section of an attachment member can also be produced from the sheet metal.

In a further, advantageous embodiment of the invention, the holder can be produced at least partially from plastic. When, for example, a storage element is produced from a plastic material, the risk of a surgical instrument and/or implant being damaged, for example, scratched when it is attached to the storage element is reduced.

Furthermore, in accordance with the invention, it is suggested that, in a surgical container of the type described at the outset, the at least one holder comprises a storage device for holding and/or storing surgical instruments and/or implants and an attachment device for attaching the holder to the container, characterized in that the attachment device can be transferred from an attaching position, in which it can be brought into engagement with and connected to the container, into a position of abutment, in which it can be brought out of engagement with the container, and that the attachment device comprises at least two attachment members connected to one another via the storage device. In this case, the holder can be brought closer to a side wall or the base within the receiving space of the container, for example, as a whole and attached thereto in a simple manner. Attachment and removal of one or more holders which are, where applicable, of different shapes can also be repeated many times.

The at least one holder is preferably one of the holders described above. They have the advantages already explained above in conjunction with the various embodiments.

It is advantageous when the container has at least one attachment surface for attaching the attachment device of the at least one holder to the container. An attachment surface can be designed, for example, to correspond to a coupling surface provided on the holder, whereby the stability of the attachment of the holder to the container is increased.

In a preferred embodiment of the invention, it may be provided for the container to have a plurality of openings which are separated from one another by at least one web and for the at least one attachment surface to be defined by at least part of a surface of a web. A surgical container with openings is easy to produce and saves on material in comparison with a container without openings. The openings can also allow liquid sterilization medium, which is found in the container following a sterilization procedure, to flow away.

The at least one web preferably has a width which corresponds to a distance between a first coupling plane and a second coupling plane of the at least one holder. During attachment of a holder to the container, a coupling element provided on an attachment member of the holder can, for example, be brought into engagement with a web such that two attachment surfaces of the web which point away from one another each abut on a coupling surface of the coupling element. The coupling element is then difficult to move and can, in particular, not be removed from the web by pressure or a pulling force exerted in a direction extending at right angles or essentially at right angles to the coupling planes.

It is favorable when the openings have a rectangular cross section. As a result, surfaces of the web pointing towards a further web have a flat form and so different parts of these surfaces are suitable as attachment surfaces, on which an abutment surface of a holder which is provided on the attachment device can abut in a stable manner.

In order to achieve a high number and a clear arrangement of the positions, at which a holder can be attached to the container, it is of advantage when the openings are arranged in a regular manner.

In a preferred embodiment of the invention, the surgical container can be designed as a sterile container. Surgical holders attached to a sterile container serve to support instruments and/or implants which are intended to be subjected to a sterilization procedure and/or to be stored in a sterile manner in the sterile container.

In a further, preferred embodiment of the invention, the surgical container is designed as a perforated basket. Surgical instruments and/or implants held on a holder attached to a perforated basket can be subjected, for example, to cleaning procedures in the perforated basket.

One embodiment of a surgical holder according to the invention for holding and/or storing surgical instruments and/or implants and provided altogether with the reference numeral 10 will be described in greater detail in conjunction with FIGS. 1 to 11. The holder 10 can be attached to a base or a side wall of a surgical container according to the invention. Two base sections 12, 14 of a base of a surgical container according to the invention are illustrated by way of example in FIGS. 1, 4, 6, 7 and 8 and these are provided with openings 16, 18 which have a rectangular cross section and are arranged in a regular manner, wherein the rectangular cross section of the openings 18 of the base section 14 is greater than the rectangular cross section of the openings 16 of the base section 12. The holder 10 can be attached to both base sections 12, 14.

A storage device 20 of the holder 10 comprises a storage element 22 for storing surgical instruments and/or implants and a holding part 24 for holding the storage element 22. The storage element 22 is produced from a plastic material and designed as a profiled bar which has essentially the shape of a flat parallelepiped. The storage element 22 is provided on a first edge surface 26 with a plurality of recesses 28 which each extend between side surfaces 30 of the storage element 22 pointing away from one another and have a profiled cross section parallel to the side surfaces 30. Surgical instruments and/or implants can be held and/or stored in the recesses 28.

In addition, the storage element 22 is provided with openings 32, each of which extends, like the recesses 28, between the side surfaces 30. The recesses 28 can be spread elastically in a longitudinal direction of the storage element 22 with a simultaneous narrowing of the openings 32. An instrument and/or implant can be introduced into a recess 28 during spreading thereof and held there in a stable manner due to the counterpressure caused by the elasticity of the storage element 22.

The holding part 24 comprises two holding members 34 in the form of flat sections of two rails 36 which extend parallel at a distance from one another, are each designed as elongated, flat, parallelepiped-shaped strips and between which the storage element 22 can be held in a holding position of the holding part 24. Edge surfaces 38 of each holding member 34 pointing towards the respectively other holding member 34 extend parallel to one another and to a mirror plane running between them, wherein the holder 10 is as a whole in mirror symmetry with respect to this mirror plane. The edge surfaces 38 define a longitudinal axis 40 of the holder 10 which is located in the mirror plane. Side surfaces 42 of the holding members 34 pointing away from the edge surfaces 38 each support over their entire extension a wing plate 44 which has essentially the form of a rectangle, the free ends of which are flattened. The wing plates 44 are bent away from the holding members 34 in a direction towards one another and are approximately parallel to the mirror plane.

In order to attach the holder 10 to a container, it has an attachment device 46 which comprises a first attachment member 48 and two second attachment members 50. The first attachment member 48 comprises an approximately square, flat base plate 52 which extends essentially at right angles to the axis 40 and a respective first end section 54 of each rail 36. The first end sections 54 of the rails 36 are bent away from the holding members 34 about a transverse axis 55 extending at right angles to the mirror plane in the direction towards the wing plates 44 of the holding members 34 and are each connected to an upper side 56 of the base plate 52 at an end surface, offset from one another. As a result, the two holding members 34 are connected to one another via the first attachment member 48. The first attachment member 48 is, therefore, angled away from the holding part 24 through a member angle of approximately 90°.

In addition, the first attachment member 48 comprises two approximately rectangular wing plates 58 which are each attached to one of two sides 60 of the base plate 52 extending at right angles to the upper side 56, are bent away from the base plate 52 in the direction towards the rails 36 and are located approximately parallel to the mirror plane. In a direction pointing away from the rails 36, the wing plates 58 of the first attachment member 48 project beyond its base plate 52. In their section projecting beyond the base plate 52, a coupling element 62 in the form of a recess is provided each time on a side bordering the base plate 52. Each recess has a first side surface 64 which points towards the rails 36, a second side surface 66 which points away from the rails 36 and a base surface 68. The second side surface 66 is located in a plane with an underside 70 of the base plate 52 likewise pointing away from the rails 36. The first side surface 64 forms a first coupling surface, the second side surface 66 a second coupling surface and the base surface 68 an abutment surface of the coupling element 62.

A corner of the wing plates 58 of the first attachment member 48, which points towards the rails 36, is flattened so that it and the corner of a wing plate 44 of a holding member 34, which is adjacent to it and likewise flattened, do not hinder one another. The corners of the wing plates 58 which point away from the rails 36 and the base plate 52 are also flattened in order to make the attachment of the first attachment member 48 to a container easier.

The second attachment members 50 each comprise a rectangular base plate 72 which extends at right angles to the axis 40 and the second end section 74 of a rail 36, wherein the respective second end section 74 is bent away from the holding member 34 in the direction towards the wing plates 44 of the holding members 34 about a transverse axis 75 extending at right angles to the mirror plane and is connected to an upper narrow side 76 of the respective base plate 72 at an end surface. As a result, the second attachment members 50 are bent away from the holding part 24 through a member angle of approximately 90° each time. In the holding position of the storage device 20, longitudinal sides 78 of the two base plates 72 of the two attachment members 50, which point towards one another, touch one another. The free space between the two rails 36 is continued by recesses in the base plates 72.

A rear surface of the base plate 72 of each second attachment member 50 bears a flat projection 80 which projects in a section beyond a lower narrow side 82 of the second attachment member 50, which is located opposite the upper narrow side 76, and the free end of which is angled approximately at right angles in the direction pointing away from the first attachment member 48. The free end of the flat projection 80 extends parallel to the rails 36.

The longitudinal side 84 of the base plate 72 of each second attachment member 50, which points away from the respectively other second attachment member 50, forms a first cathetus side of a wing plate 86 which is angled away from the base plate 72 in the direction towards the first attachment member, is approximately parallel to the mirror plane, has the form of a right-angled triangle and the hypotenuse side of which points towards the adjacent rail 36. A second cathetus side 88 of the wing plate 86 extends in a plane with the lower narrow side 82 of the base plate 72 and has a projection 90 pointing away from the rails 36 at its free end.

The flat projection 80, the section of the base plate 72 comprising the lower narrow side 82 and the section of the wing plate 86 comprising the second cathetus side 88 form a coupling element 92 of the second attachment member 50. In this respect, a surface 94 of the free end of the flat projection 80, which points towards the rails 36, forms a first coupling surface, the lower narrow side 82 of the base plate 72 and the second cathetus side 88 of the wing plate 86 form a second coupling surface and a surface 96 of the section of the flat projection 80 projecting beyond the base plate 72 points away from the first attachment member 48 and forms an abutment surface of the coupling element 92.

The attachment members 48, 50 and the holding members 34 are, as a result, connected securely to one another. They can be worked in one piece and be produced, for example, by way of deformation out of a flat model which can be generated in one punching step from a flat metal sheet.

Figure 4:
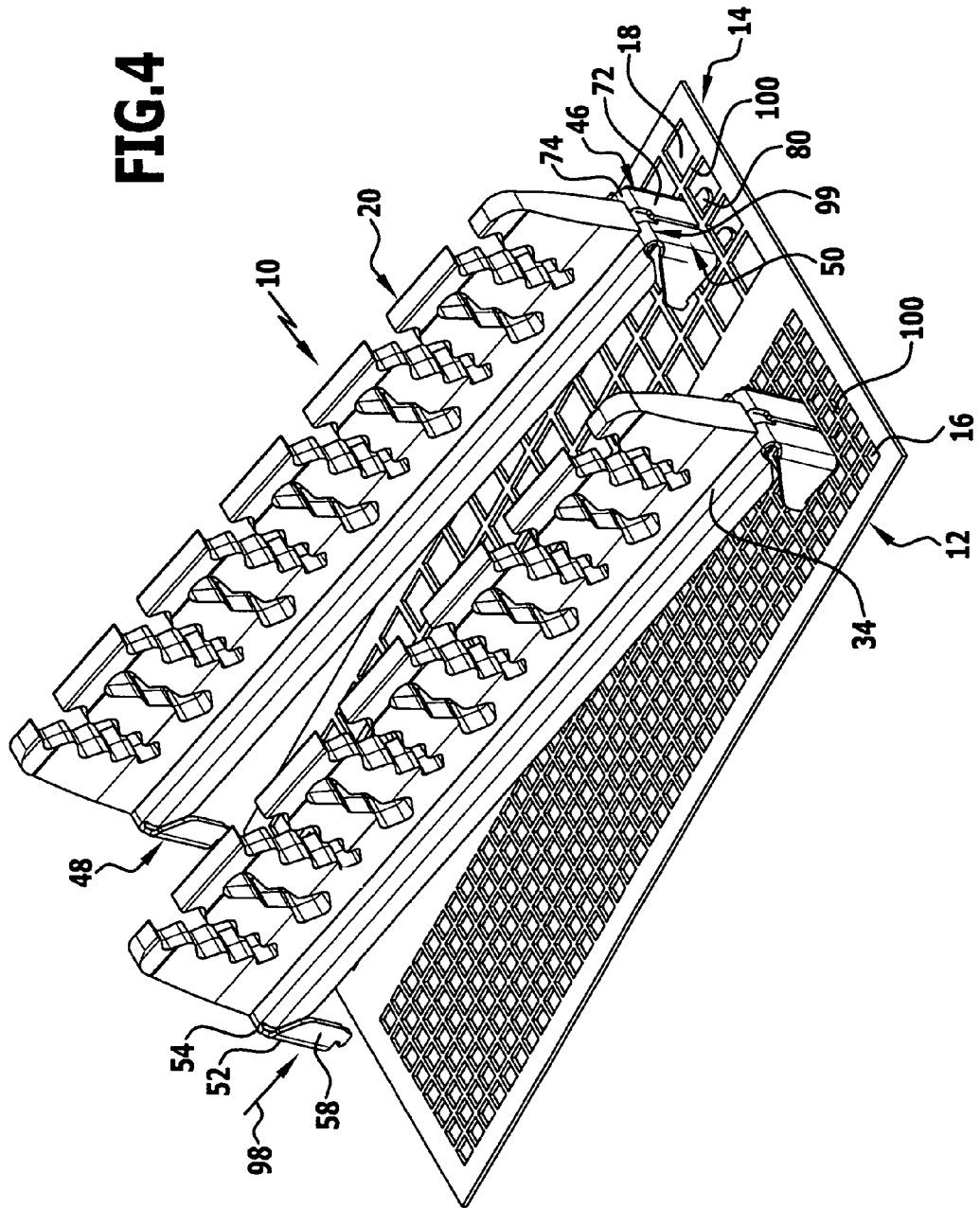
FIG. 4: shows a perspective view of the holders from FIG. 1 during attachment thereof to the base.

In order to attach the holder 10 to a base section 12, 14 of a surgical container, the two flat projections 80 of the second attachment members 50 can, first of all, as illustrated in FIG. 4, be guided through openings 16, 18 of the respective wall section 12, 14. In the case of attachment to the wall section 14 with larger openings 18, the two flat projections 80 are guided through adjacent openings 18, in the case of attachment to the wall section 12 with smaller openings 16, two openings 16 are used, between which an additional opening 16 is located.

The attachment device 46 can be transferred from an attaching position into a position of abutment in that pressure is exerted on the base plate 52 of the first attachment member 48 in a direction 98 parallel to the longitudinal axis 40 towards the second attachment members 50. The end sections 54, 74 of the rails 36 connect the base plates 52, 72 of the respective attachment members 48, 50 to the holding members 34 in an elastically resilient manner. The attachment members 48, 50 can, therefore, be deflected by pressure in the direction 98 relative to the holding members 34, wherein a distance between the free end of the first attachment member 48 and the free ends of the second attachment members 50 is reduced. It is possible, as a result of the distance being reduced, to also guide the sections of the wing plates 58 of the first attachment member 48 which project beyond the base plate 52 through a respective opening 16, 18. Guidance, in particular, through one of the smaller openings 16 of the wall section 12 is made easier in that the corner of the wing plate 58 pointing away from the rails 36 and the base plate 52 is flattened and the section of the wing plate 58 to be guided through the opening 16 is, therefore, narrowed.

Subsequently, the elastically resilient end sections 54, 74 of the rails 36 can be used as restoring elements. They define together a restoring device 99 of the holder 10. As soon as the pressure is taken from the base plate 52 of the first attachment member 48, the attachment members 48, 50 are moved back into the attaching position by the spring force. In this respect, all the coupling elements present come into engagement with webs 100 each extending between two openings 16, 18.

The elasticity of the restoring elements can be ensured in a particularly simple manner in that the attachment members 48, 50 and the holding members 34 are formed in one piece by being punched out of a sheet of spring steel and subsequently deformed.

Figure 5:
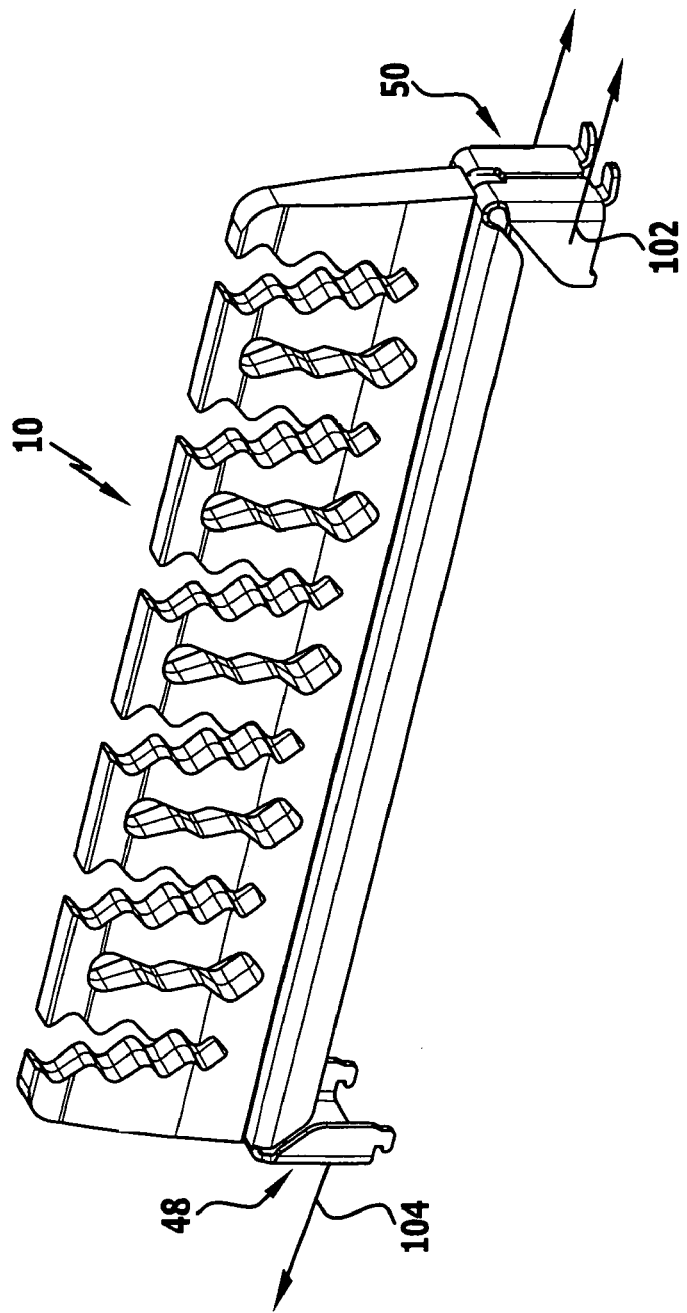
FIG. 5: shows a perspective view of one of the holders from FIG. 1 during subsequent securing to the base.

The transfer of the attachment device 46 from the position of abutment into the attaching position can be aided by additional securing, as illustrated schematically in FIG. 5. A pulling force directed away from the second attachment members 50 in a direction 102 parallel to the longitudinal axis 40 is exerted on the first attachment member 48, on the second attachment members 50 a pulling force directed away from the first attachment member 48 in a direction 104 parallel to the longitudinal axis.

Figure 6:
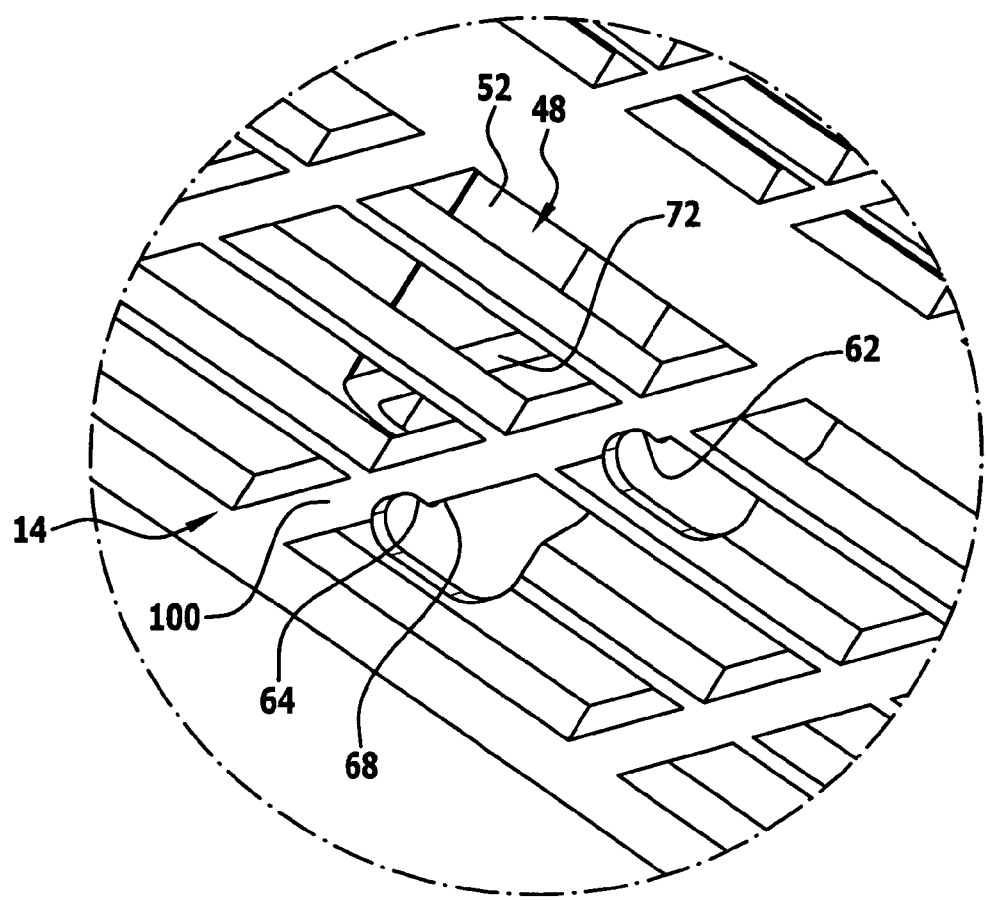
FIG. 6: shows a perspective view from below of a first attachment member of the respective holders from FIG. 1, attached to the base.

As illustrated in FIG. 6 by way of example for a holder 10 attached to the base section 14, each coupling element 62 of the first attachment member 48 is in engagement with a web 100. In this respect, its first side surface 64, which defines the first coupling surface, lies on an underside of the web 100 pointing away from the rails 36 and its second side surface 66, which defines the second coupling surface, on an upper side of the web 100 pointing towards the rails 34. Additional stability is obtained in that the underside 72 of the base plate 52 also rests in sections on an additional web 100.

Figure 7:
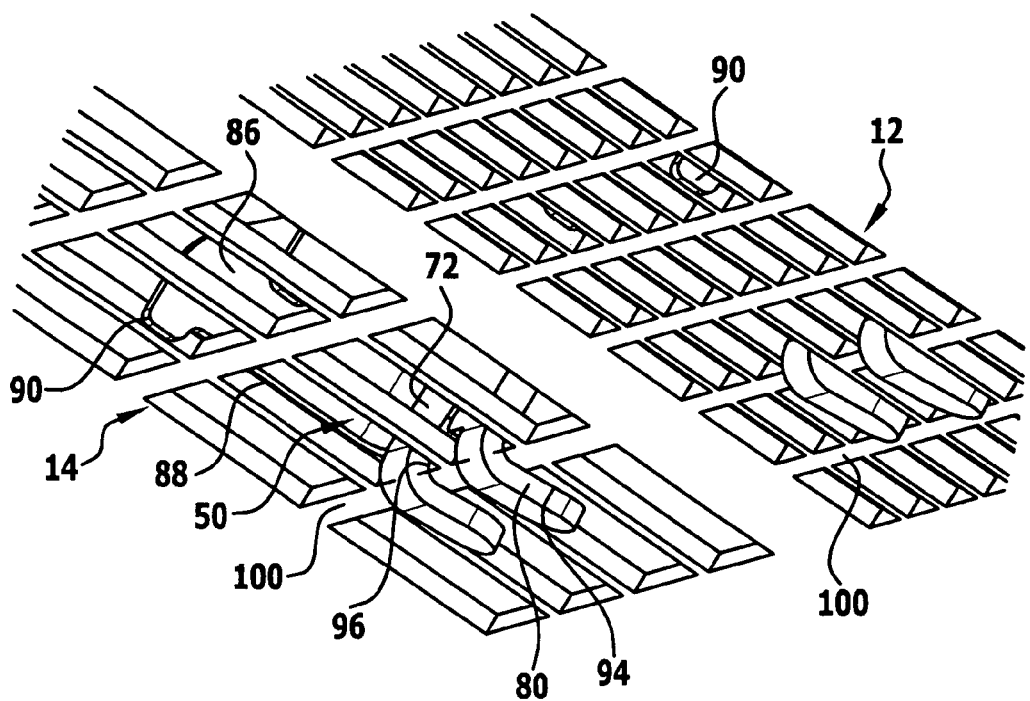
FIG. 7: shows a perspective view from below of a second attachment member of one of the holders from FIG. 1, attached to the base.

As illustrated in FIG. 7, when a holder 10 is attached to a container the surfaces 94 of the free ends of the flat projections 80 of the second attachment members 50, which define the first coupling surfaces, each abut, in addition, on a surface of a web 100 pointing away from the rails 34. The lower narrow sides 82 of the base plates 72 and the second cathetus sides 88 of the wing plates 86 of the second attachment members 50, which together define the second coupling surfaces, abut on surfaces of the webs 100 pointing towards the rails 34. As a result of this attachment of the coupling elements of the holder 10 to webs 100, any removal of the holder 10 from the respective base section 12, 14 as a result of any pulling on the holder 10 in a direction extending at right angles to the respective base section 12, 14 is not possible.

A further increase in the stability of the attachment of the holder 10 to the container is achieved in that the attachment members 48, 50 each have an abutment surface which abuts on a surface of a web 100 pointing towards an adjacent web 100 in the attaching position of the attachment device 46. In the case of the first attachment member 48, the abutment surface is the base surface 68 of the coupling element 62, in the case of the second attachment members 50 the surface 96 of the flat projection 80 pointing away from the first attachment member 48. Each abutment surface secures the holder 10 against any slipping or sliding in a direction pointing towards the respective abutting web surface. Since the abutment surfaces of the first attachment member 48 and the abutment surfaces of the second attachment members 50 point in opposite directions, any movement of the holder 10 due to a pulling force or pressure exerted along the axis 40 is made more difficult for as long as the attachment device remains in the attaching position.

Figure 8:
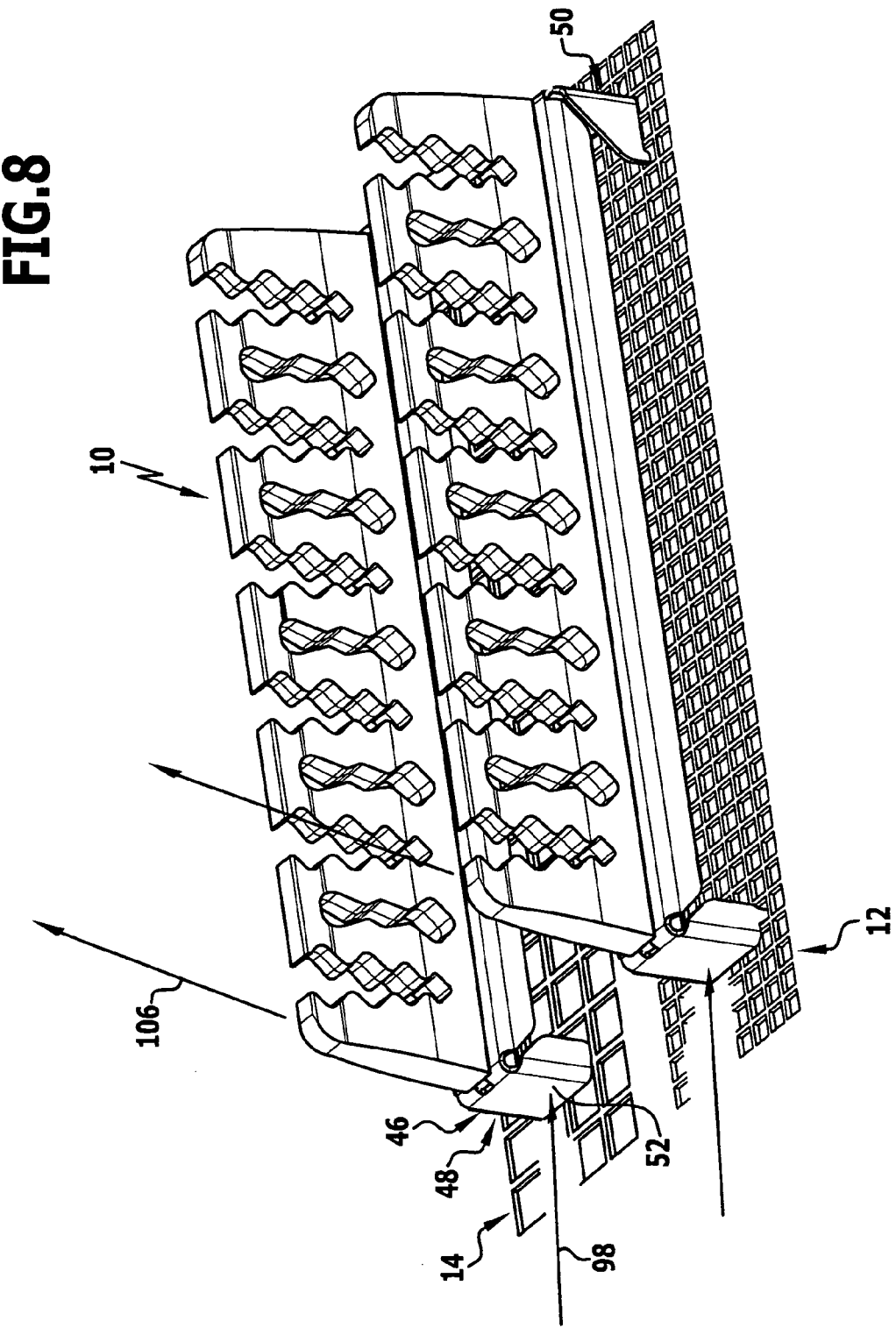
FIG. 8: shows a perspective view of the holders from FIG. 1 during removal from the base.

In order to be able to remove the holder 10 from the container, the attachment device 46 must be transferred first of all, as illustrated in FIG. 8, from the attaching position into the position of abutment again in that pressure is exerted on the base plate 52 of the first attachment member 48 in the direction 98. While the attachment device is in the position of abutment, first of all the first attachment member 48 and, subsequently, the second attachment members 50 can be removed from the container by means of a pulling force on the holder 10 in a direction 106 pointing away from the respective wall section 12, 14.

Particularly in the case of attachment to a base section 12 with smaller openings 16, the holder 10 is protected by the projections 90 provided on the wing plates 86 of the second attachment members 50 from being transferred into the position of abutment by means of pressure on the second attachment members 50 in the direction towards the first attachment member 48 and, therefore, from being removable from the container. As shown, for example, in FIG. 6, the projections 90 each engage in an opening 16. The second attachment members 50 cannot be deflected in the direction of the first attachment member 48 to such an extent that the flat projections 80 could be guided out through openings 16 since the projection 90 pushes against a web 100 before that. As a result, the first attachment member 48 must be removed from the base section 12 first of all.

Figure 9:
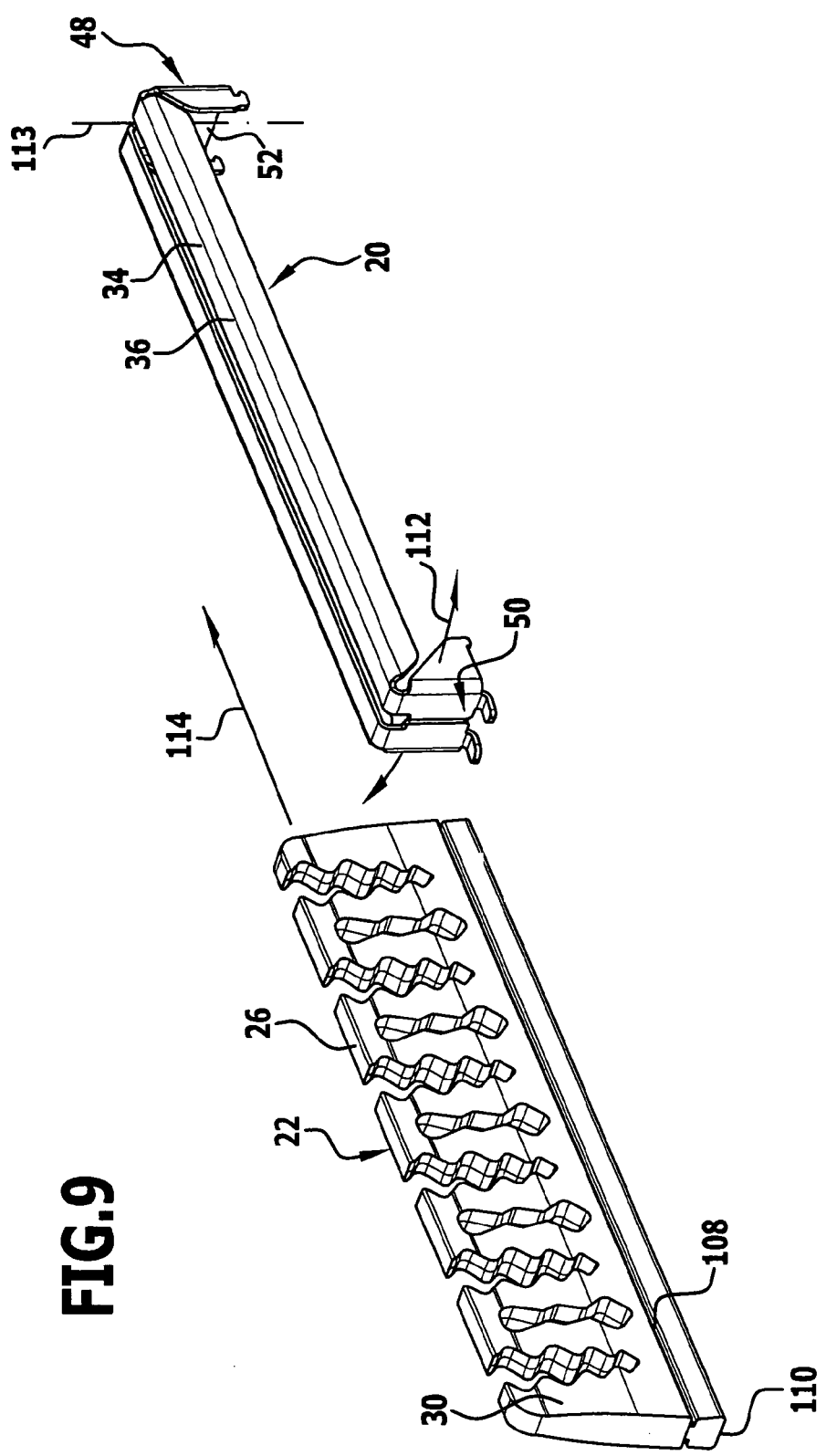
FIG. 9: shows a perspective view of one of the holders from FIG. 1 in the state of separation of the storage element from the holding part.
Figure 10:
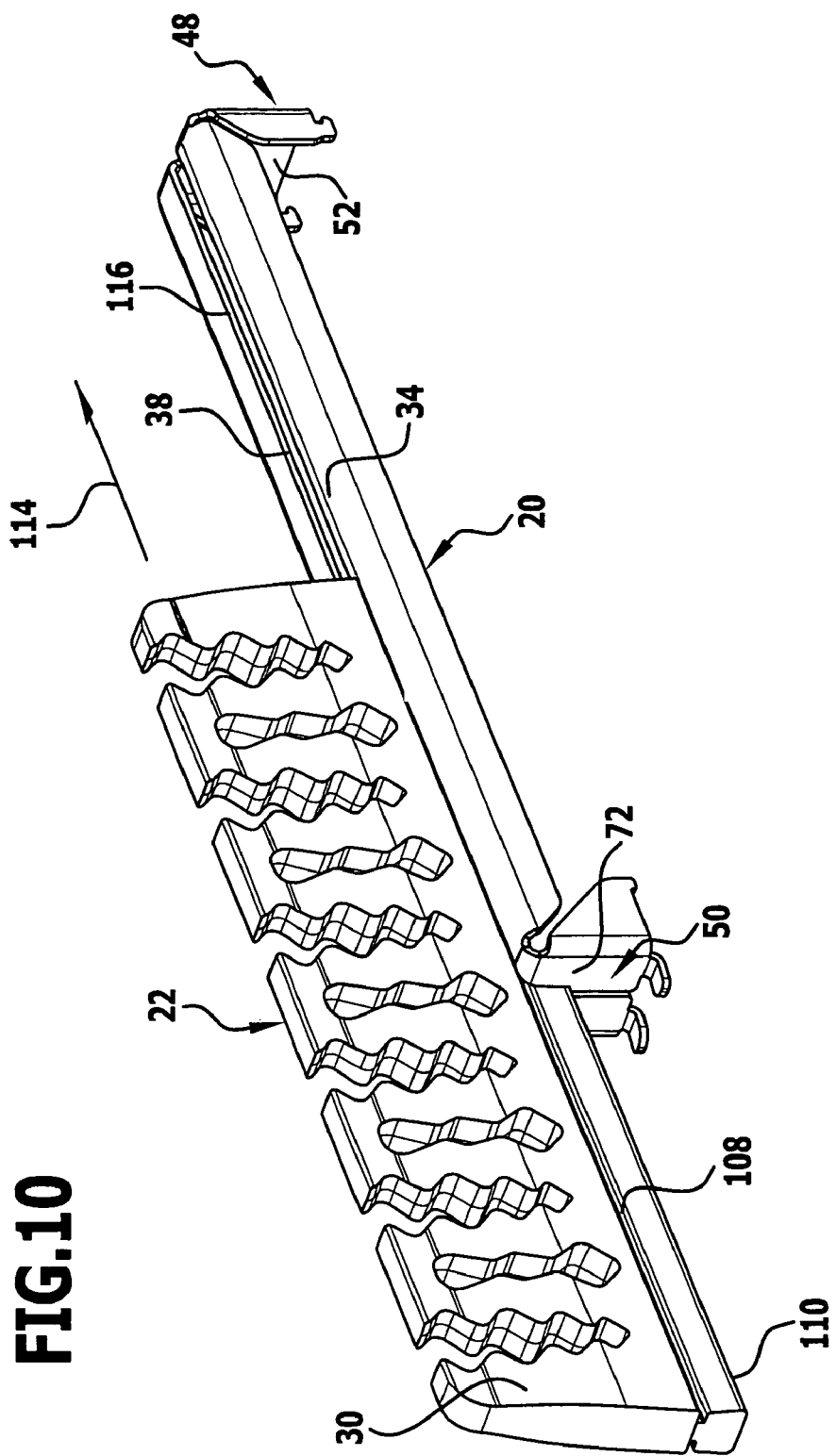
FIG. 10: shows a perspective view of one of the holders from FIG. 1 during connection of the storage element and the holding part.
Figure 11:
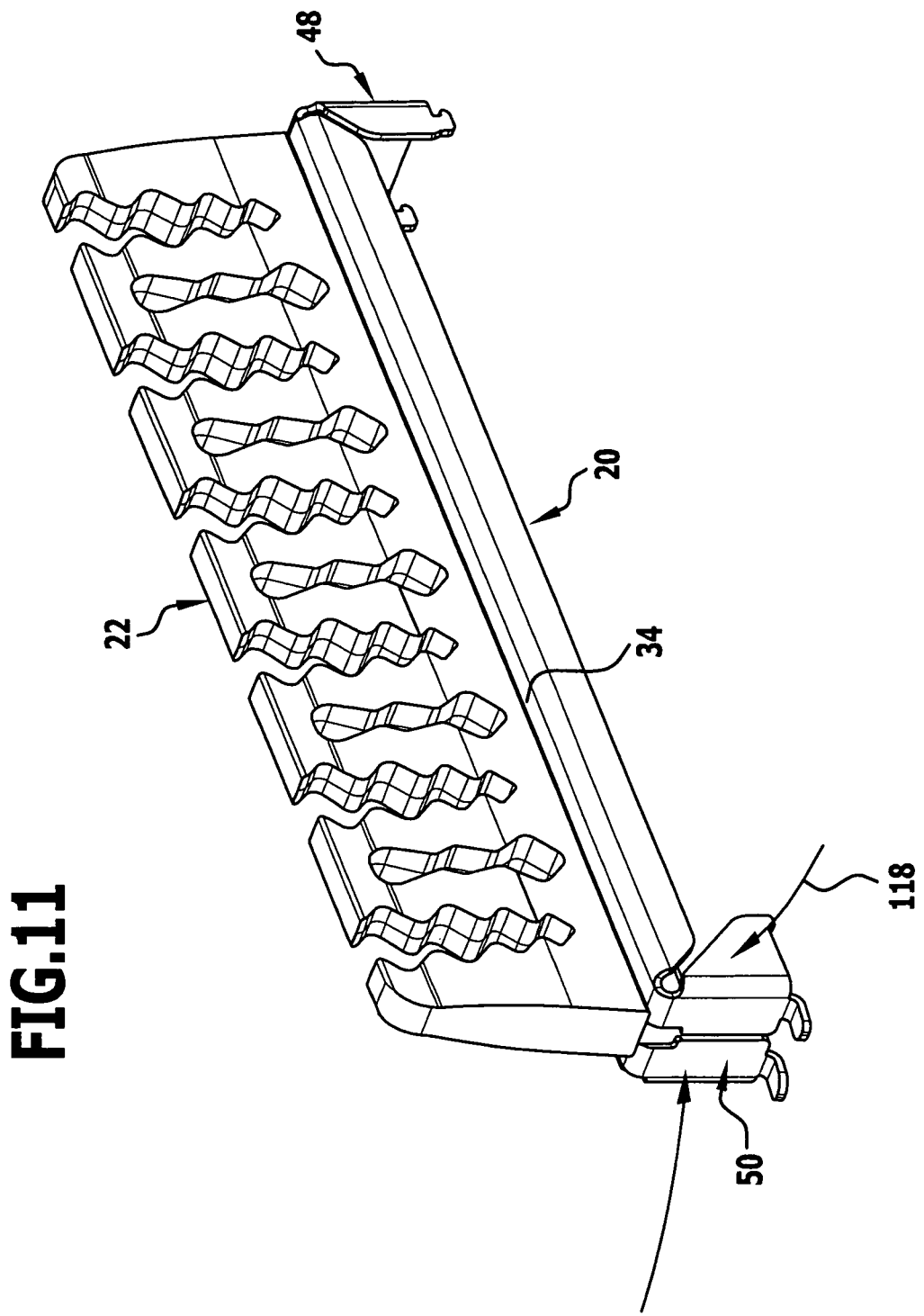
FIG. 11: shows a perspective view of one of the holders from FIG. 1 during attachment of the storage element to the holding part.
Figure 12:
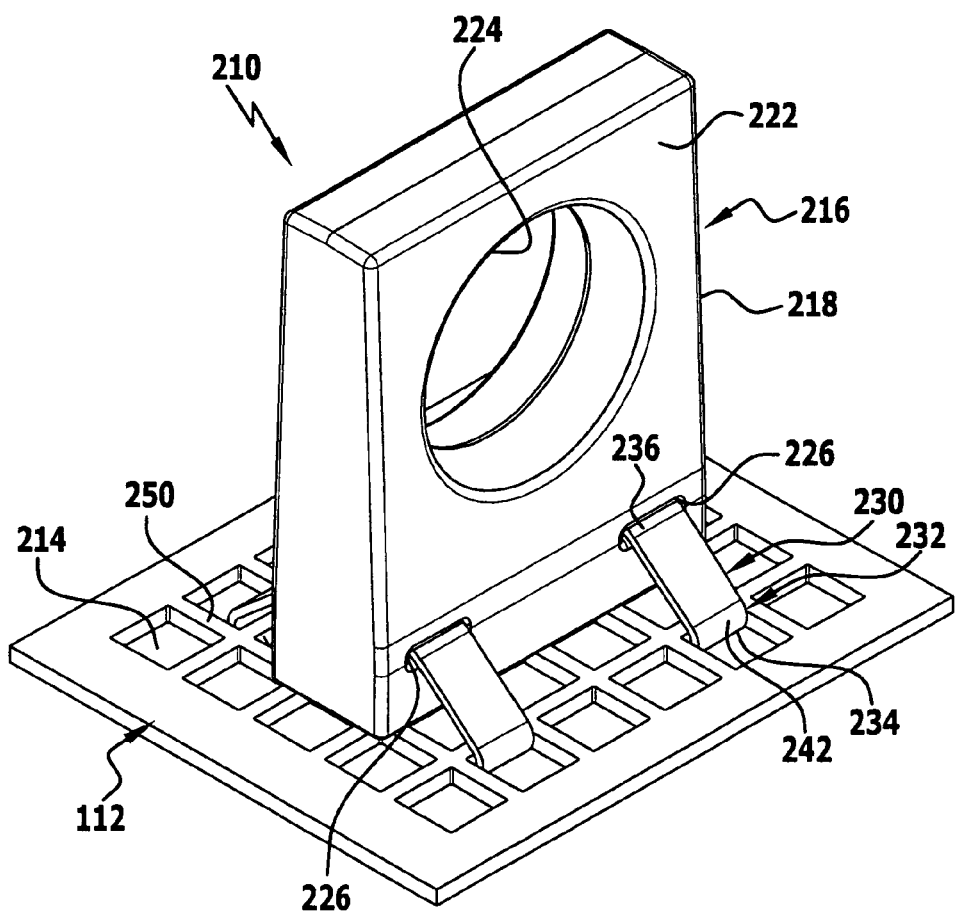
FIG. 12: shows a perspective view of a second embodiment of a surgical holder according to the invention attached to a base of a surgical container according to the invention.
Figure 13:
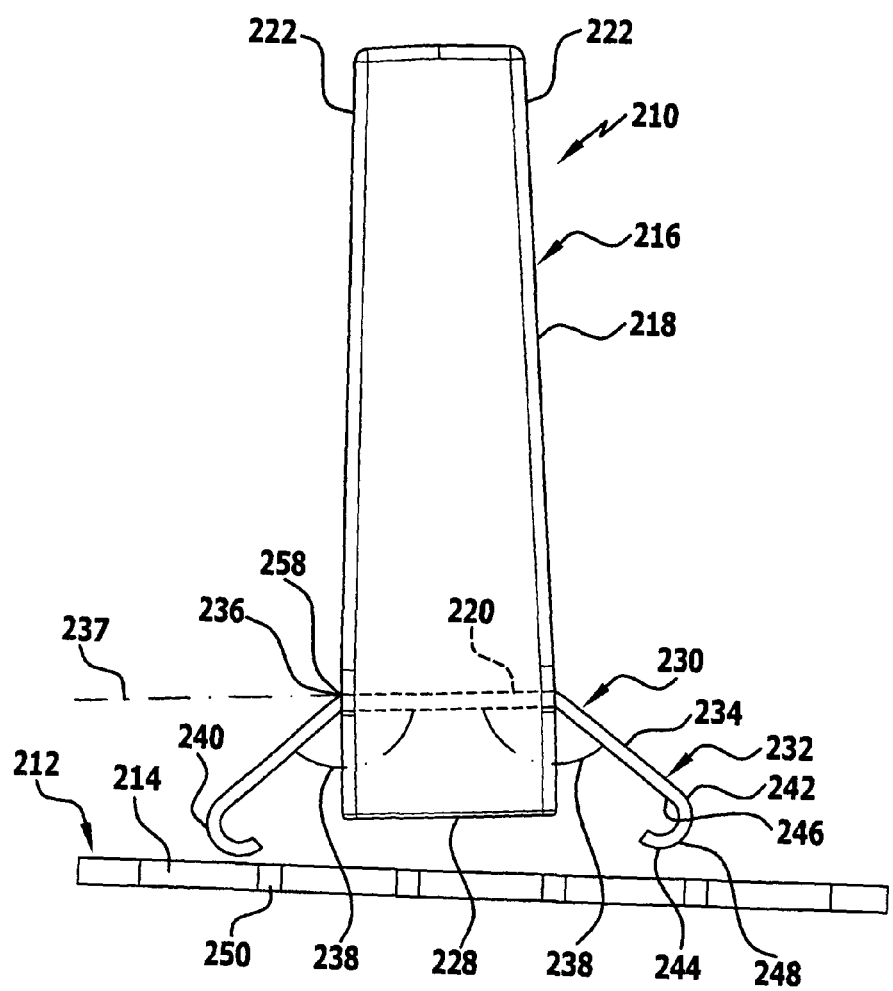
FIG. 13: shows a view of an end side of the holder illustrated in FIG. 12 in the state of separation of the holder from the base.

FIGS. 9 to 11 show the procedure for attaching the storage element 22 to the storage device 20 located first of all in a holding position. On each of its respective side surfaces 30, the storage element 22 has a connecting element which extends over an entire length of the side surface 30 in the form of a groove 108. Both grooves 108 extend at the same distance parallel to a second edge surface 110 of the storage element 22 which points away from the first edge surface 26.

The storage device 20 is brought out of the holding position into a removal position in that the two second attachment members 50 are moved in directions 112 away from one another and are pivoted about a bending axis 113 extending through the base plate 52 of the first attachment member 48 and lying in the mirror plane of the holder 10. As a result, the distance between the two rails 36 and, therefore, between the two holding members 34 is also increased. The base plate 52 of the first attachment member 48 is bent slightly along the bending axis 113.

The storage element 22 can now be guided between the two holding members 34 in a direction 114 parallel to the axis 40. In this respect, each groove 108 will be guided to in front of an edge section 116 of a holding member 34 which is provided with the edge surface 38 and designed as a holding element.

The sections of the side surfaces 30 of the storage element 22 located between the grooves 108 and the second edge surface 110 will be guided through a free space between the two base plates 72 of the two attachment members 50.

While the storage device 20 is still in the removal position, the storage element 22 can be brought into loose engagement with the holding members 34. As a result, it can be moved in the direction 114 in a simple manner but be deflected into other directions only with difficulty.

When the storage element 22 is positioned between the holding members 34 over the entire extension of its length, the edge surfaces 38 of the edge sections 116 each point towards a side surface 30 of the storage element 22. The storage device 20 can now be transferred back into the holding position due to pivoting movement of the second attachment members 50 towards one another, each in a direction 118. The edge sections 116 then engage in the grooves 108 in a form-locking and force-locking manner and the storage element 22 is secured in the storage device 20.

To remove the storage element 22 from the holding part 24, it must be transferred back into the removal position first of all. This is made difficult or is possible when the holder 10 is attached to a container. Since, in this case, the attachment members 48, 50 are in engagement with webs 100 of the container, any movement of the two attachment members 50 relative to one another will be made more difficult or prevented in the same way as any bending of the base plate 72 of the second attachment member 50. As a result, the storage element 22 is held securely in the holding part 24 when the holder 10 is attached to a container.

In contrast to, for example, the holder described in DE 20 2005 015 415 U1, during the attachment of which to a container an attachment element is brought closer to a base of the container from an outer side of the container and a profiled element from an inner side thereof and only then connected to one another, the holder 10 can be brought closer to a base section 12 or 14 from one side of the base section 12 or 14, i.e., for example, within the receiving space of the container and be attached to it as a whole, i.e., with a storage element 22 connected to the holding part 24, as shown in FIG. 4. In this respect, the storage element which is preferably produced from a plastic material is attached to the holding members 34 which are securely connected to the attachment members 48, 50 and preferably produced in one piece with the attachment members 48, 50 from a spring stainless steel sheet. Normally, the second attachment members 50 are guided with one hand and the first attachment member 48 with the other hand towards the respective base sections 12 or 14 and secured to them during attachment of the holder 10. Additional handling is not necessary during the attachment of the holder 10, in particular, no connection of several parts of the holder 10 to one another. These advantages result, in particular, from the fact that the attachment members 48, 50 are connected to one another via the storage device 20.

In FIGS. 12 to 16, a second embodiment of a surgical holder according to the invention for holding and/or storing surgical instruments and/or implants is illustrated and provided with the reference numeral 210. In addition, a base section 212 of a base of a surgical container according to the invention is illustrated in FIGS. 12 to 16, wherein the holder 210 can be attached to the base section 212. The base section 212 is provided with openings 214 arranged in a regular manner and having a rectangular cross section.

A storage device 216 of the holder 210 comprises a storage element 218 for holding and/or storing surgical instruments and/or implants and a holding part 220 for holding the storage element 218. The storage element 218 is produced from a plastic material, for example, silicone and has essentially the shape of a flat parallelepiped. An opening 224 with a circular cross section extends between two side surfaces 222 of the storage element 218 which point away from one another. An implant can, for example, be accommodated in the opening 224 for storage purposes.

In addition, the storage element 218 has two holding part openings 226 which likewise extend between the side surfaces 222, have a cross section in the form of a flat rectangle and are spaced at the same distance from an edge surface 228 of the storage element 218.

Each holding part 220 of the holder 210 is designed in the form of a web and is defined by a flat, central section of a strip 230 preferably produced from a metal, in particular, spring steel. One holding part 220 is guided each time through a holding part opening 226 of the storage element 218 so that the storage element 218 is held at the holding parts 220.

The holder 210 can be attached to a container by means of an attachment device 232. The attachment device 232 comprises four attachment members 234, wherein two attachment members 234 are connected to one another each time via a holding part 220. Each attachment member 234 is defined by an outer section of the strip 230 and has an elastically resilient connecting section 236, via which it is connected to the holding part 220. Two attachment members 234 are positioned in front of each of the side surfaces 222 of the storage element 218.

The flat holding part 220 of the strip 230 defines a holding part plane 237. The two attachment members 234 connected to the holding part 220 are bent towards one another away from the holding part 220 and out of the holding part plane 237. A member angle 238 between the holding part 220 and an attachment member 234 connected to it is approximately 135° each time.

Each attachment member 234 comprises a free end of a strip 230. This free end is bent over through approximately 180° in a direction away from the holding part plane 237 and towards the second attachment member 234 connected to the same holding part 220 and defines a coupling element 240, 242 of the attachment member 234. Each attachment member 234 therefore has the shape of a hook which is open towards the second attachment member 234 connected to the same holding part 220.

Two side surfaces of each coupling element 240, 242 which point towards one another define two coupling surfaces 244, 246, wherein a first coupling surface 244 points essentially towards the storage device 216 and a second coupling surface 246 points essentially away from the storage device 216.

A surface of each coupling element 240, 242, which is arranged between the first coupling surface 244 and the second coupling surface 246 and extends essentially at right angles to the first coupling surface 244 and the second coupling surface 246, defines an abutment surface 248.

The holding part 220 and the attachment members 234 connected to it, including the coupling elements 240, 242, are worked in one piece and can be generated in a simple manner, for example, from a flat metal strip by way of multiple bending.

Figure 14:
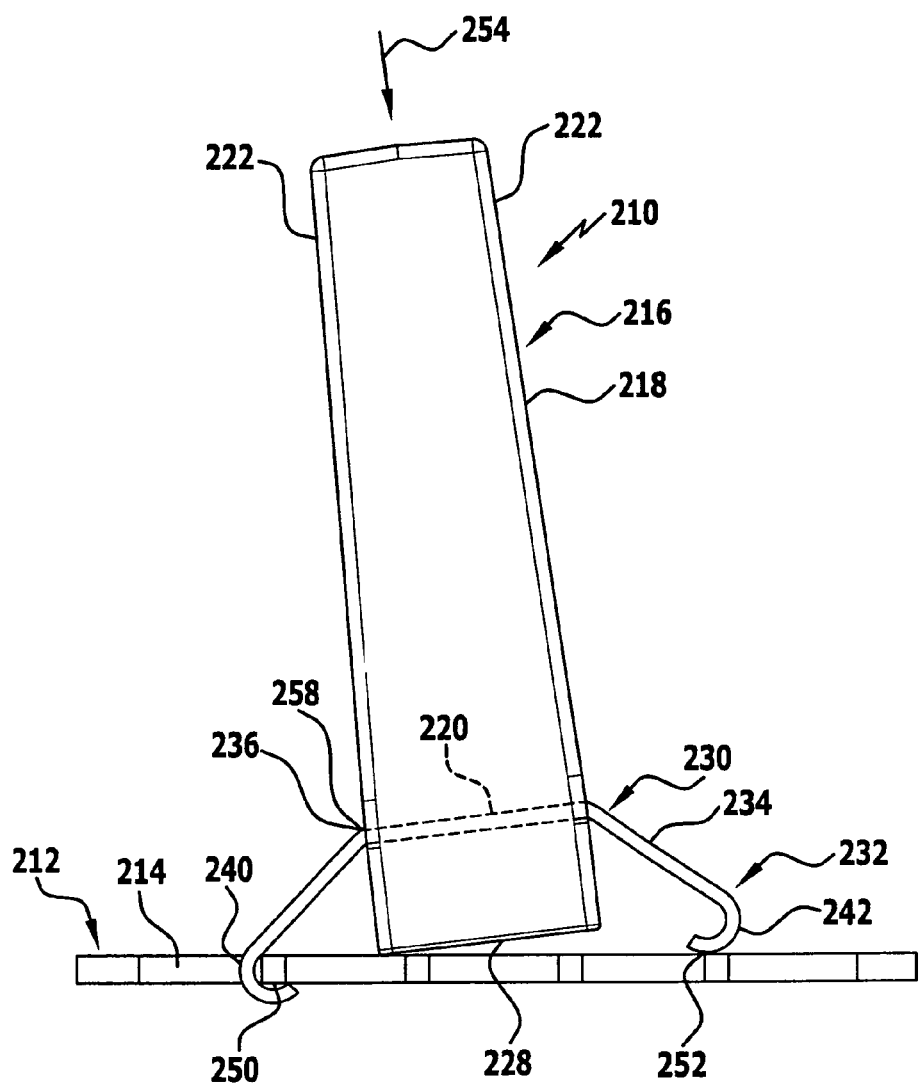
FIG. 14: shows a view of an end side of the holder illustrated in FIG. 12 during attachment thereof to the base.
Figure 15:
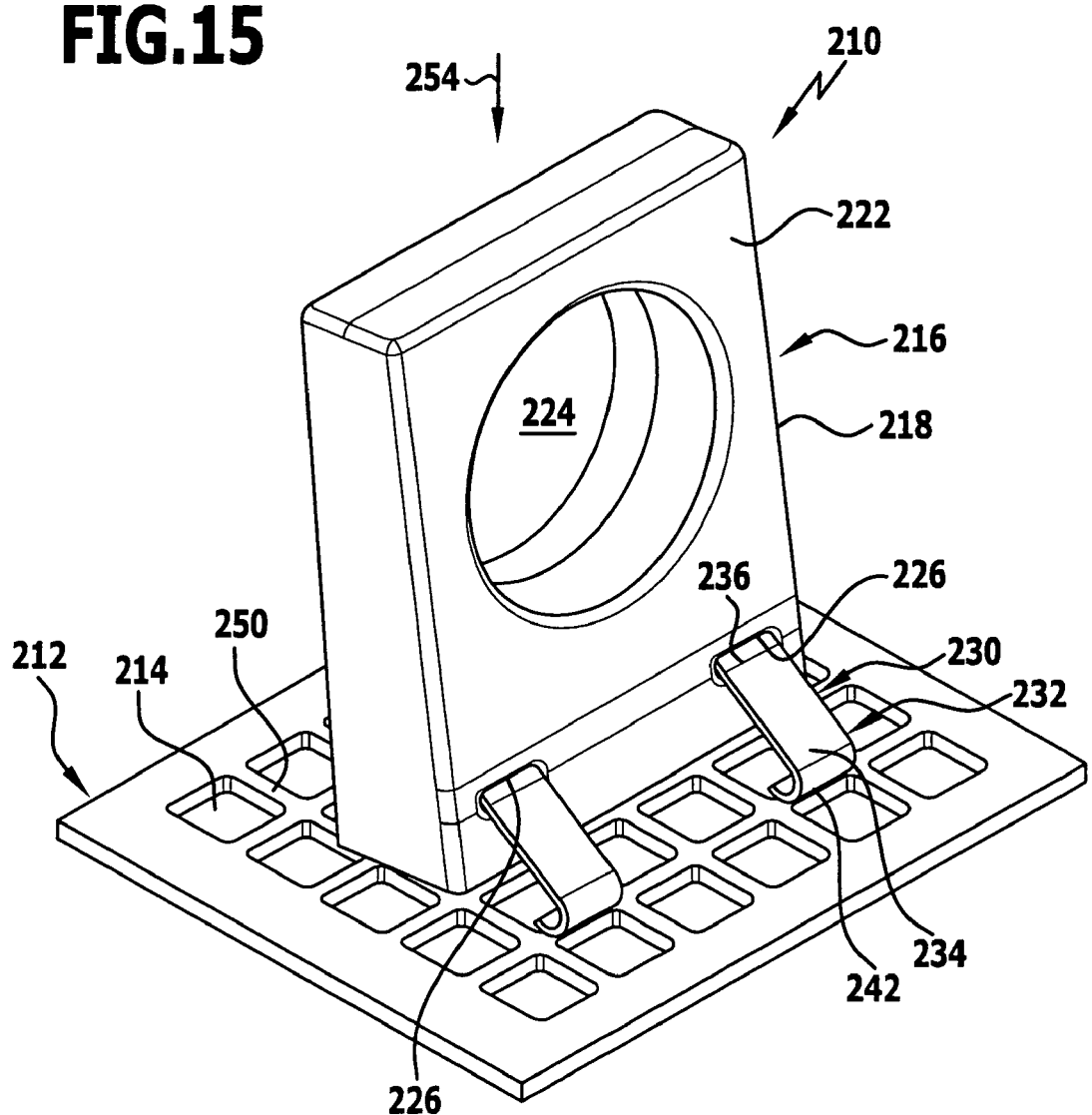
FIG. 15: shows a perspective view of the holder illustrated in FIG. 12 during attachment thereof to the base.

In order to attach the holder 210 to the base section 212 of a surgical container, first coupling elements 240 of the two hook-like attachment members 234, which are arranged in front of one of the two side surfaces 222 of the storage element 218, can each be guided first of all, as illustrated in FIGS. 14 and 15, through an opening 214 in the base section 212. The first coupling elements 240 guided through the opening 214 are each brought into engagement with a web 250 extending between two openings 214 so that the first coupling surface 240 abuts on an underside of the web 250 pointing away from the storage device 216 and the second coupling surface 242 abuts on an upper side of the web 250 pointing towards the storage device 216. The abutment surface 248 of the coupling element 240 abuts on a surface of the web 250 pointing towards an adjacent web 250. The hook-like attachment members 234 which comprise the first coupling elements 240 are each hooked to a web 250.

Second coupling elements 242 of the two attachment members 234 arranged in front of the other side surface 222 of the storage element 218 cannot likewise be guided through an opening 214 for as long as the attachment device 232 remains in the attaching position because they are each positioned in front of a web 250 and cannot be guided past it.

The attachment device 232 can now be transferred into the position of abutment as a result of pressure on the attachment members 234 and/or the storage element 218 in a direction 254 towards the base section 212. The first coupling elements 240 which have already been guided through openings 214 and abut on webs 250 remain in engagement with these webs 250 while outer surfaces 252 of the second coupling elements 243 glide over the surface of the web 250, in front of which they are each arranged. In this respect, the member angles 238 and a distance between the respective two attachment members 234 connected to one another via a holding part 220 are increased. As a result of this process, the attachment device 232 is transferred into the position of abutment, in which each of the second coupling elements 242 can also, finally, be guided through an opening 214.

The two elastically resilient connecting sections 236 of the attachment members 234 each define a restoring element of the holder 210 and, therefore, together a restoring device 258 of the holder 210. Once the two coupling elements 242 have been guided through the openings 214, the member angles 238 will be reduced again by the spring force, the distance between the two coupling elements 242 and the first coupling elements 240 will become smaller. Each of the second coupling elements 242 is also brought into engagement with the web 250, on which its outer surface 252 has slid during attachment, by way of snapping in. Each of the hook-like attachment members 234, which comprise the two coupling elements 242, is also now hooked to a web 250.

The hook-like attachment members 234 of the holder 210 may be locked to the webs 250 of the container in the manner described simply with the aid of the restoring device 258. While the hook of each attachment member 234 of the holder 210 is open towards the second attachment member 234 connected to the same holding part 220, hook-like attachment members, each of which is open pointing away from a second attachment member connected to the same holding part, can also be provided in additional embodiments. Such an embodiment of a holder can be attached, for example, to a container in that member angles are reduced in size in a position of abutment in comparison with an attaching position.

The stability of the attachment of the holder 210 to the container is increased further in that the edge surface 228 of the storage element 218 also abuts on the surfaces of a plurality of webs 250.

Figure 16:
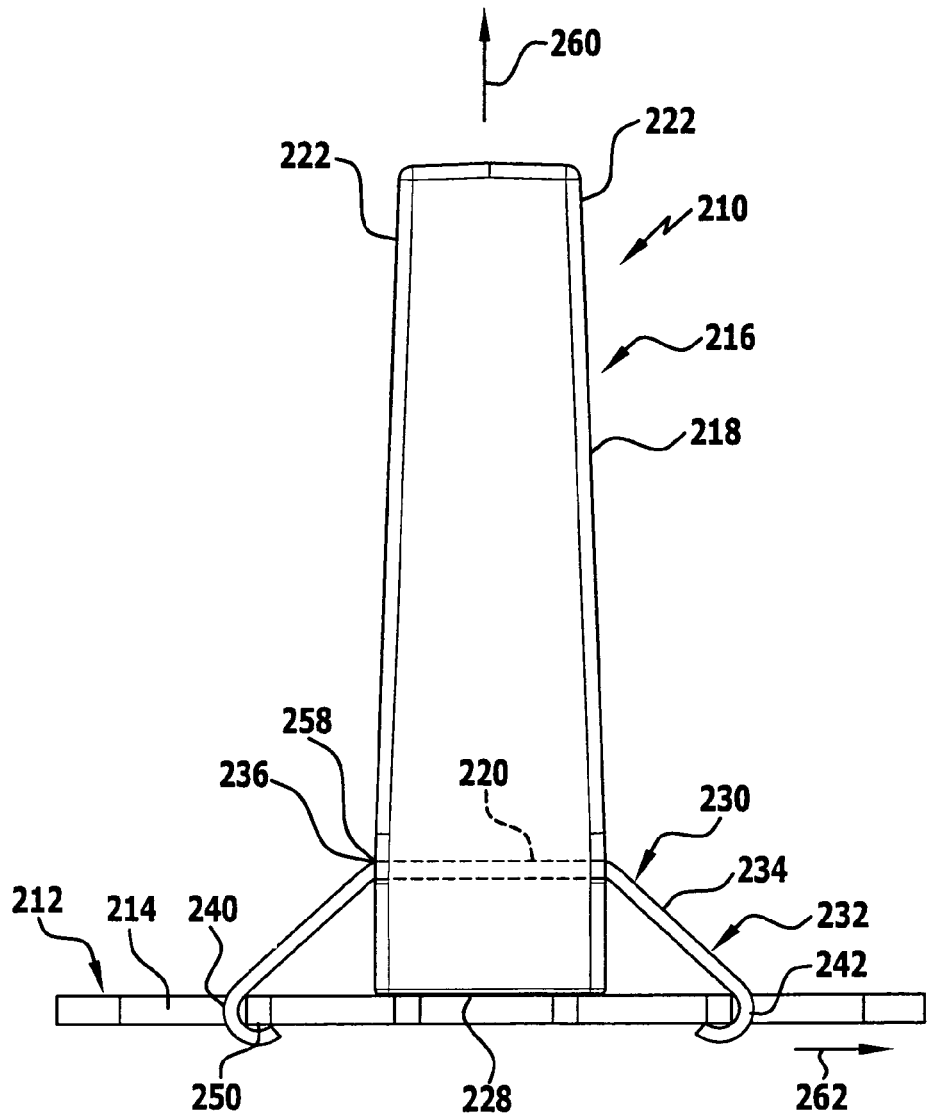
FIG. 16: shows a side view of the holder from FIG. 12 attached to the base.

As illustrated in FIG. 16, the holder 210 attached to the base section 212 cannot be removed from the container by a pulling force on the storage element 218 or the attachment members 234 in a direction 260 pointing away from the base section 212 on account of the first coupling surfaces of the coupling elements 240, 242 abutting on the undersides of the webs 250. Due to the abutment of the abutment surfaces 248 of the coupling elements 240, 242 on corresponding attachment surfaces of the webs 250, the holder 210 is also protected against any slipping or sliding in a direction pointing towards the respective attachment surface.

It is necessary to transfer the attachment device 232 from the attaching position into the position of abutment in order to remove the holder 210 from the base section 212. For this purpose, the parts, for example, of the second coupling elements 242 which abut on undersides of webs 250 can be moved in a direction 262 pointing away from the first coupling elements 240, wherein the position of the first coupling elements 240 remains unaltered and the member angles 238 are increased in size. Once the position of abutment is reached, the second coupling elements 242 can be guided through the openings 214. The attachment device 232 is subsequently transferred back into the attaching position by the restoring device 258 and the holder 210 can be removed from the base section 212 as a result of the first coupling elements 240 also being removed from the respective web 250 and the first coupling elements 240 being guided through the openings 214.

The storage element 218 can be releasably connected to the holding parts 220. It can then be removed from the holding parts 220 in that the holding parts 220 are guided out of the holding part openings 226. In this respect, an attachment member 234 is also guided through the holding part opening 226 each time with the coupling element 240, 242 provided on it.

During the connection of the storage element 218 to a holding part 220, an attachment member 234 is guided first of all through a holding part opening 226 and, subsequently, the holding part 220 is guided into the holding part opening 226.

The storage element 218 can also be securely connected to the holding parts 220. In this case, the entire holder 210 consists of a single component which can be obtained, for example, by sheathing the strips 230 with the plastic of the storage element 218.

The strip 230, the different sections of which define the holding part 220 and the attachment device 232 in the holder 210 illustrated in FIG. 12 to FIG. 16, can also, itself, define a complete holder according to the invention. In contrast to the holder 210, its central section does not, in this case, define a holding part 220 for holding a storage element but rather serves itself as a storage device for holding and/or storing surgical instruments and/or implants. This one-piece holder can be attached to a base or a side wall of a surgical container without any interaction with additional components, such as, for example, a storage element. The same mechanism as in the case of the holder 210 can be used for the attachment and the removal of the holder on the container. For example, surgical instruments, implants, cables, circuit boards or small motors can be held and/or stored, for example, clamped between the web-like storage device of this holder and a base section, to which it is attached. As a result, the strips 230 which are preferably manufactured from spring steel have manifold uses.

In a further embodiment of the holder according to the invention, a storage device suitable for holding and/or storing surgical instruments and/or implants can be obtained as a result of further processing of the central section of the strip 230, for example, by deforming or sheathing it with a plastic material.

The holder 210 can be attached to a base section 212 of a container as a whole, i.e., with a storage element 218 connected to the holding parts 220 with a simple manipulation. The attachment members 234, which are connected to one another via the storage device 216, can be brought towards the base section 21 from one side thereof and attached to it. In this respect, the first coupling elements 240 first of all and, subsequently, the second coupling elements 242 are each brought into engagement with a web 250. These steps can be carried out with one hand quickly one after the other.

Figure 17:
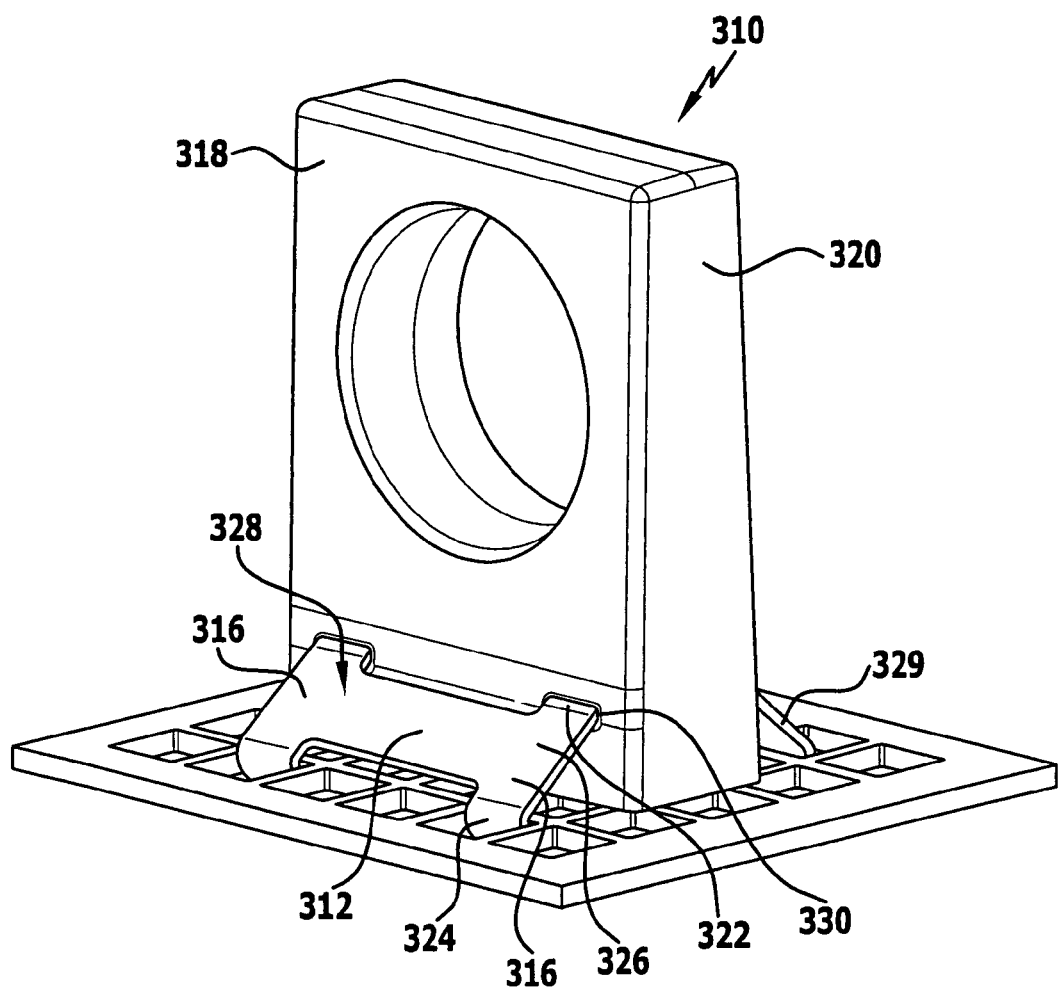
FIG. 17: shows a perspective view of a third embodiment of a surgical holder according to the invention attached to a base of a surgical container according to the invention.

A third embodiment of a surgical holder according to the invention for surgical instruments and/or implants for a surgical container is illustrated in FIG. 17. The various elements which the holder 310 comprises are identical to the elements of the holder 210 described in FIG. 12 to FIG. 16. However, a stabilizing element 312 is provided, in addition, in the case of the holder 310. It connects two attachment members 316, which are connected to different holding parts, to one another, wherein the connected attachment members 316 are arranged in front of the same side surface 318 of a storage element 320 held on the holding parts. The stabilizing element 312 extends between sides, which point towards one another, of respective sections 326 of the two attachment members 316 which are arranged between a connecting section 322 and a coupling element 324. Instead of the two strips 230 of the holder 210 which are separate from one another, the holder 310 comprises a component 328 which is worked in one piece. It comprises two holding parts, two respective attachment members 316, 329 connected to each holding part and the stabilizing element 312. The component 328 can be produced by punching a flat model from a metal sheet and subsequently bending the model. It is preferably produced from spring stainless steel.

The storage element 320 can be releasably connected to the component 328. The storage element 320 can then be mounted on the holding parts in that two attachment members 329 which are not connected to one another via the stabilizing element 312 and, subsequently, the holding parts connected to them are each guided through a holding part opening 330 of the storage element 320. Removal of the storage element 320 from the holding parts 314 is carried out by guiding the holding parts 314 first of all and, subsequently, the attachment members 329 not connected to one another via the stabilizing element 312 out of the holding part openings 330.

The use of the component 328 offers the advantage that only two individual parts need be used for the attachment of the storage element 320 to the holding parts and, in particular, both holding parts can be connected to the storage element 320 in one go. In addition, a greater stability results for the attachment of the holder 310 to a container.

Alternatively thereto, the storage element 320 can also be securely connected to the component 328 in the case of the holder 310.

The component 328 can not only form a holder 310 in conjunction with a storage element 320 but also define a holder according to the invention independently, like the strip 230 described above. In this respect, the sections of the component 328 defining the holding parts in the case of the holder 310 are used themselves as a storage device.

While preferred embodiments of the invention have been shown and described herein, it will be understood that such embodiments are provided by way of example only. Numerous variations, changes and substitutions will occur to those skilled in the art without departing from the scope of the invention. Accordingly, it is intended that the appended claims cover all such variations as fall within the scope of the invention.

What is claimed is:

1. Surgical holder for at least one of surgical instruments and implants for a surgical container, comprising:
 a storage device adapted for at least one of holding and storing at least one of surgical instruments and implants, and an attachment device adapted for attaching the holder to the container, said attachment device being transferable from an attaching position into a position of abutment, said attachment device being adapted to be brought into engagement with and connected to the container in said attaching position, said attachment device being adapted to be brought out of engagement with the container in said abutment position, said attachment device comprising at least two attachment members for attaching the holder to the container, said attachment members being connected to one another via the storage device, the storage device comprising at least one storage element and at least one holding part, said at least one storage element being adapted for at least one of holding and storing the at least one of surgical instrument and implants, said at least one holding part being adapted for holding the at least one storage element and being transferable from a holding position into a removal position, the at least one storage element being held on the at least one holding part in said holding position, the at least one storage element and the at least one holding part being detachable from one another in said removal position, wherein:
the attachment device and the holding part are transferable independently from one another: (a) from the attaching position into the position of abutment; and (b) from the holding position into the removal position, the at least one holding part comprises at least two holding members, the at least two holding members being pivotable relative to one another about a first pivot axis extending through one of the at least two attachment members and transverse to at least one of the at least two holding members, and the at least two holding members pivot open about the first pivot axis to accept the storage element.

2. Holder as defined in claim 1, wherein at least one of the at least two attachment members is arranged so as to be movable relative to at least one of the storage device and another of the at least two attachment members.

3. Holder as defined in claim 1, wherein the attachment members protrude from the storage device.

4. Holder as defined in claim 1, wherein a restoring device is provided for transferring the attachment device from the position of abutment into the attaching position.

5. Holder as defined in claim 4, wherein the restoring device comprises at least one restoring element for transferring the attachment device from the position of abutment into the attaching position, said element being associated with one of the at least two attachment members.

6. Holder as defined in claim 5, wherein the at least one restoring element is designed in the form of an elastically resilient section of the attachment member.

7. Holder as defined in claim 1, wherein a distance between the at least two attachment members is greater or smaller in the position of abutment than in the attaching position.

8. Holder as defined in claim 7, wherein the distance is defined between free ends of the at least two attachment members.

9. Holder as defined in claim 1, wherein:
at least one of the at least two attachment members comprises at least one coupling element,
the at least one coupling element has a first coupling surface for abutment on a corresponding attachment surface of a surgical container, said first coupling surface pointing towards or essentially towards the storage device, and
the holder has at least one second coupling surface for abutment on at least one corresponding attachment surface of a surgical container, said second coupling surface pointing away or essentially away from the storage device.

10. Holder as defined in claim 9, wherein:
the first coupling surface defines a first coupling plane and the second coupling surface defines a second coupling plane,
the first and the second coupling planes are parallel or essentially parallel to one another, and
the first coupling plane is at a greater distance from the storage device than the second coupling plane.

11. Holder as defined in claim 9, wherein:
the at least one coupling element is designed in the form of a recess with a first side surface, and
the first side surface defines the first coupling surface.

12. Holder as defined in claim 9, wherein:
the at least one coupling element is designed in the form of a projection with a first side surface, and
the first side surface defines the first coupling surface.

13. Holder as defined in claim 9, wherein:
the at least one coupling element is designed in the form of a curved free end of the at least one attachment member, and
the curved free end has a first side surface and the first side surface defines the first coupling surface.

14. Holder as defined in claim 9, wherein the at least one second coupling surface is provided on the at least one coupling element.

15. Holder as defined in claim 14, wherein:
the at least one coupling element is designed in the form of one of a recess, a projection or a curved free end of the at least one attachment member and has a second side surface, and
the second side surface defines the at least one second coupling surface.

16. Holder as defined in claim 9, wherein the attachment device has at least one abutment surface extending at right angles or essentially at right angles to at least one of the first and the second coupling surface and is adapted to abut on a corresponding attachment surface of the container in the attaching position.

17. Holder as defined in claim 16, wherein the at least one abutment surface is provided on at least one attachment member.

18. Holder as defined in claim 1, wherein the at least two attachment members are connected to one another via the at least one holding part.

19. Holder as defined in claim 18, wherein the at least one holding part is arranged between the at least two attachment members.

20. Holder as defined in claim 18, wherein at least one of the at least two attachment members is angled away from the at least one holding part through a member angle.

21. Holder as defined in claim 20, wherein the member angle is approximately 20° to approximately 160°.

22. Holder as defined in claim 1, wherein the at least two holding members each have a first end and a second end and are connected to one another at their first ends via a hinged connection.

23. Holder as defined in claim 22, wherein the hinged connection is designed in the form of one of a simple hinge, a film hinge or a spring hinge.

24. Holder as defined in claim 22, wherein one attachment member comprises the hinged connection.

25. Holder as defined in claim 22, wherein an attachment member is arranged at the second end of at least one of the at least two holding members.

26. Holder as defined in claim 1, wherein at least one of the at least two holding members has at least one holding element for holding the at least one storage element in the holding position in at least one of a form-locking and a force-locking manner.

27. Holder as defined in claim 26, wherein the at least one holding element points towards or essentially towards another of the at least two holding members.

28. Holder as defined in claim 26, wherein the at least one holding element is designed in the form of a projection.

29. Holder as defined in claim 26, wherein the at least one holding element is designed in the form of a recess.

30. Holder as defined in claim 26, wherein at least one of the at least two holding members is designed in the form of a profiled rail.

31. Holder as defined in claim 1, wherein the at least one storage element has at least one connecting element held on the at least one holding part in the holding position in at least one of a form-locking and a force-locking manner.

32. Holder as defined in claim 31, wherein the at least one connecting element is designed to correspond to a holding element.

33. Holder as defined in claim 31, wherein the at least one connecting element is designed in the form of one of a projection or a recess.

34. Holder as defined in claim 33, wherein the at least one connecting element is designed in the form of a groove.

35. Holder as defined in claim 1 wherein the at least one storage element is designed in the form of a profiled bar.

36. Holder as defined in claim 1, wherein the at least one holding part and the at least two attachment members are connected non-releasably.

37. Holder as defined in claim 36, wherein the at least one holding part and the at least two attachment members are worked in one piece.

38. Holder as defined in claim 1, wherein the holder is produced at least partially from a metal.

39. Holder as defined in claim 1, wherein the holder is produced at least partially from a plastic material.

40. Holder as defined in claim 1, wherein:
   at least one of the at least two attachment members is pivotable about a second pivot axis with respect to the holding part; and
   the second pivot axis is perpendicular to the first pivot axis.

41. Surgical container for at least one of the storage and sterilization and cleaning of at least one of surgical instruments and implants, comprising:
   a receiving space defined by a base and side walls, and
   at least one holder for at least one of surgical instruments and implants,
   the at least one holder comprising a storage device and an attachment device,
   the storage device being adapted for at least one of holding and storing the at least one of surgical instruments and implants, and
   the attachment device being adapted for attaching the holder to the container and being transferable from an attaching position into a position of abutment, said attachment device being adapted to be brought into engagement with and connected to the container in said attaching position, said attachment device being adapted to be brought out of engagement with the container in said abutment position, and
   the attachment device comprising at least two attachment members connected to one another via the storage device,
   the storage device comprising at least one storage element and at least one holding part, said at least one storage element being adapted for at least one of holding and storing the at least one of surgical instrument and implants,
   said at least one holding part being adapted for holding the at least one storage element and being transferable from a holding position into a removal position, the at least one storage element being held on the at least one holding part in said holding position, the at least one storage element and the at least one holding part being detachable from one another in said removal position,
   wherein:
   the attachment device and the holding part are transferable independently from one another: (a) from the attaching position into the position of abutment; and (b) from the holding position into the removal position, and
   the at least one holding part comprises at least two holding members, the at least two holding members being pivotable relative to one another about a first pivot axis extending through one of the at least two attachment members and transverse to at least one of the at least two holding members, and
   the at least two holding members pivot open about the first pivot axis to accept the storage element.

42. Surgical container as defined in claim 41, wherein the container has at least one attachment surface for attaching the attachment device of the at least one holder to the container.

43. Surgical container as defined in claim 42, wherein:
   the container has a plurality of openings separated from one another by at least one web, and
   the at least one attachment surface is defined by at least part of a surface of a web.

44. Surgical container as defined in claim 43, wherein the at least one web has a width corresponding to a distance between a first coupling plane and a second coupling plane of the at least one holder.

45. Surgical container as defined in claim 43, wherein the openings have a rectangular cross section.

46. Surgical container as defined in claim 43, wherein the openings are arranged in a regular manner.

47. Surgical container as defined in claim 41, wherein the container is designed as a sterile container.

48. Surgical container as defined in claim 41, wherein the container is designed as a perforated basket.

49. Surgical container as defined in claim 41, wherein:
   at least one of the at least two attachment members is pivotable about a second pivot axis with respect to the holding part; and
   the second pivot axis is perpendicular to the first pivot axis.

* * * * *